United States Patent
Carlson et al.

(10) Patent No.: US 6,569,685 B1
(45) Date of Patent: May 27, 2003

(54) PROTEIN FINGERPRINT SYSTEM AND RELATED METHODS

(75) Inventors: Robert H. Carlson, Union City, CA (US); Ian E. Burbulis, Kensington, CA (US); Roger Brent, Berkeley, CA (US)

(73) Assignee: The Molecular Sciences Institute, Inc., Berkeley, CA (US)

( * ) Notice: Subject to any disclaimer, the term of this patent is extended or adjusted under 35 U.S.C. 154(b) by 0 days.

(21) Appl. No.: 09/412,732

(22) Filed: Oct. 5, 1999

(51) Int. Cl.$^7$ .................. G01N 21/62; G01N 21/63; G01N 21/64; G01N 33/68

(52) U.S. Cl. .................. 436/86; 436/166; 436/171; 436/172

(58) Field of Search .................. 435/4; 530/300, 530/350, 345, 402, 410; 436/8, 15, 86, 87, 88, 56, 63, 166, 171, 172

(56) References Cited

U.S. PATENT DOCUMENTS

| | | | |
|---|---|---|---|
| 4,979,824 A | 12/1990 | Mathies et al. | 356/318 |
| 5,087,558 A | 2/1992 | Webster, Jr. | 435/5 |
| 5,188,934 A | 2/1993 | Menchen et al. | 436/455 |
| 5,510,240 A | 4/1996 | Lam et al. | 435/7.1 |
| 5,525,479 A | 6/1996 | Anthony et al. | 435/15 |
| 5,527,684 A | 6/1996 | Mabile et al. | 435/7.1 |
| 5,667,975 A | 9/1997 | Dykstra et al. | 435/6 |
| 5,716,852 A | 2/1998 | Yager et al. | 436/172 |
| 5,770,455 A | 6/1998 | Cargill et al. | 436/518 |
| 5,800,994 A | 9/1998 | Martinelli et al. | 435/6 |
| 5,800,995 A | 9/1998 | Patonay et al. | 435/6 |
| 5,830,666 A | 11/1998 | Fujita et al. | 435/6 |
| 5,834,250 A | 11/1998 | Wells et al. | 435/7.1 |
| 5,846,821 A | 12/1998 | Guerinot et al. | 435/320.1 |
| 5,856,082 A | 1/1999 | Aebersold et al. | 435/4 |
| 5,866,331 A | 2/1999 | Singer et al. | 435/6 |
| 5,885,840 A | 3/1999 | Kamentsky et al. | 436/63 |

FOREIGN PATENT DOCUMENTS

WO    WO 97/07205    2/1997    .......... C12N/15/10

OTHER PUBLICATIONS

Chou, H. P., et al., "A Microfabricated Device for Sizing and Sorting DNA Molecules," 96(1) Proc. Natl. Acad. Sci. 11–13 (1999).

Cohen, B. A., et al., "An Artificial Cell–Cycle Inhibitor Isolated From a Combinatorial Library," 95(24) Proc. Natl. Acad. Sci. 14272–77 (Nov. 1998).

Colas, P., et al., "Genetic Selection of Peptide Aptamers That Recognize and Inhibit Cyclin– Dependent Kinase 2," 380 Nature 548–50 (Apr. 11, 1996).

(List continued on next page.)

*Primary Examiner*—Jeffrey E. Russel
(74) *Attorney, Agent, or Firm*—TraskBritt, PC

(57) ABSTRACT

A system and method for characterizing protein molecules. A protein molecule of interest is isolated from other types of protein molecules. The protein molecule of interest is modified to a one-dimensional structure from the natural three-dimensional structure of the protein molecule. Each of a first type of amino acid residue of the protein molecule is labeled with a first tag. Each of a second type of amino acid residue of the protein molecule is labeled with a second tag. The first and second tags impart to the protein molecule a detectable set of characteristic ancillary properties that facilitates distinction of the protein molecule of interest from other types of protein molecules. When these ancillary properties are detected, a fingerprint of the protein molecule is revealed. A listing of known protein molecules and of the fingerprints corresponding to each of the known protein molecules serves as a library to facilitate identification of unknown proteins. A fingerprint of a protein molecule of interest determined in the same manner as the fingerprints of known proteins listed in the library is compared with fingerprints of the known protein molecules to identify the protein molecule of interest.

51 Claims, 12 Drawing Sheets

OTHER PUBLICATIONS

Deniz, A., et al., "Single–Pair Fluorescence Resonance Energy Transfer on Freely Diffusing Molecules: Observation of Forster Distance Dependence and Subpopulations," 96(7) Proc. Natl. Acad. Sci. 3670–75 (Mar. 1999).

Glazer, A.N., "The Chemical Modification of Proteins by Group–Specific and Site Specific Reagents," in The Proteins 1–103 (H. Neurath, et al. eds., 1976).

Guttman, A., "Capillary Sodium Dodecyl Sulfate–Gel Electrophoresis of Proteins," 17 Electrophoresis 1333–41 (1996).

Guttman, A., "On the Separation Mechanism of Capillary Sodium Dodecyl Sulfate–Gel Electrophoresis of Porteins," 16 Electrophoresis 611–16 (1995).

Ha, T., et al., "Single–Molecule Fluorescence Spectroscopy of Enzyme Conformational Dynamics and Cleavage Mechanism.," 96(3) Proc. Natl. Acad. Sci. 893–98 (Feb. 1999).

Haugland, R. P., Handbook of Fluorescent Probes and Research Chemicals 45 (M. Spence, ed., 1996).

Ju, J., et al., "Fluorescence Energy Transfer Dye–Labeled Primers for DNA Sequencing and Analysis," 92 Proc. Natl. Acad. Sci. 4347–51 (May 1995).

Miller, J.H., "Experiment 48: Assay of locate β–Galacosidase," Experiments in Molecular Genetics (1972).

Pau, C.P., et al., "A Rapid Enzymatic Procedure for 'Fingerprinting' Bacteria by Using Pattern Recognition of Two–Dimensional Fluorescence Data," 32 Clin. Chem. 987–6 (1986).

Stix, G., "Parsing Cells," Sci. Am. 35–36 (Jul. 1999).

Stryer, L., et al., "Energy Transfer: A Spectroscopic Ruler," 58 Proc. Natl. Acad. Sci. 719–26 (1967).

Trinchieri, G., "Interleukin–12: A Cytokine Produced by Antigen–Presenting Cells with Immunoregulatory Functions in the Generation of T–Helper Cells Type 1 and Cytotoxic Lymphokines," 84 Blood 4008–27 (Dec. 15, 1994).

Weiss, J., "Fluorescence Spectroscopy of Single Biomolecules," 283 Science 1676–83 (Mar. 12, 1999).

Wickramasinghe, H.K., "Scanned–Probe Microscopes," 261 Sci. Am. 74–81 (Oct. 1989).

Carlson, Robert H, et al., "Activation and Sorting of Human White Blood Cells," 1(1) Biomed. Microdevices 39–47 (1998).

Carlson, Robert H, et al., "Self–Sorting of White Blood Cells in a Lattice," 79(11) Physical Rev. Let. 2149–52 (1997).

Carlson, Robert H., "Deformation Activation of Human Leukocytes" (1997).

Doolittle, R.F., "Redundancies in Protein Sequence" in *Predictions of Protein Structure and the Principles of Protein Conformation* 599–623 (Gerald D. Fasman, ed., 1989).

Ha, T., et al., "Hindered Rotational Diffusion and Rotational Jumps of Single Molecules," 80(10) Physical Rev. Let. 2093–96 (1998).

Kirley, Terence L., "Reduction and Fluorescent Labeling of Cysteine–Containing Proteins," 180 Analytical Biochem. 231–236 (1989).

Knight, James B., et al., "Hydrodynamic Focusing on a Silicon Chip: Mixing Nanoliters in Microseconds," 80(17) Physical Rev. Let. 3863–66 (1998).

LaVallie, Edward R., et al., "A Thioredoxin Gene Fusion Expression System That Circumvents Inclusion Body Formation in the *E. coli* Cytoplasm," 11(2) Biotechnology 187–93 (1993).

Meldal, Morten, "Properties of Solid Support" in SolidPhase Peptide Synthesis, 289 Methods in Enzymology 83–104 (Gregg B. Fields, ed., 1997).

Richardson, Jane S., et al., "Principles and Patterns of Protein Conformation" in *Predictions of Protein Structure and the Principles of Protein Conformation* 1–98 (Gerald D. Fasman, ed., 1989).

Songster, Michael F., et al., "Handles for Solid–Phase Peptide Synthesis" in *Solid–Phase Peptide Synthesis*, 289 Methods in Enzymology 126–74 (Gregg B. Fields, ed., 1997).

Weigl, Bernhard H., et al., "Optical and Electrochemical Diffusion–Based Detection of Analytes in Complex Samples Using Microfabricated Flow Structures," 3606 SPIE 82–89 (Proceedings of the SPIE Conference on Micro– and Nanofabricated Structures and Devices for Biomedical Environmental Applications II, Jan. 1999).

White, Frederick H. Jr., "Regeneration on Enzymatic Activity by Air–Oxidation of Reduced Ribonuclease with Observations of Thiolation During Reduction with Thioglycolate," 235(2) J. Biological Chem. 383–89 (1960).

Wong, Shan S., "Reactive Groups of Proteins and Their Modifying Agents" in *Chemistry of Protien Conjugation and Cross–Linking* 7–48 (1991).

Wong, Shan S., "Homobifunctional Cross–Linking Reagents" in *Chemistry of Protein Conjugation and Cross–Linking* 75–145 (1991).

Fisher, Carl A., et al., "Lipid Binding–Induced Conformational Changes in the N–Terminal Domain of Human Apolipoprotein E," 40 Journal of Lipid Research 93–99 (1999).

Jona, Istvan, et al., "Structural Dynamics of the $Ca^{2+}$–ATPase of Sarcoplasmic Reticulum. Temperature Profiles of Fluorescence Polarization and Intramolecular Energy Transfer," 1028 Biochimica et Biophysica Acta 183–199 (1990).

Lillo, M. Pilar, et al., "Design and Characterization of a Multisite Fluorescence Energy–Transfer System for Protein Folding Studies: A Steady–State aad Time–Resolved Study of Yeast Phosphoglycerate Kinase," 36 Biochemistry 11261–11272 (1997).

Nakajima, Kunio, et al., "Optical Processing by Scanning Near–Field Optical/Atomic Force Microscopy," 273 Thin Solid Films 327–330 (1996).

"After the Genome," The Economist Technology Quarterly 27–29 (Dec. 9, 2000).

Zor, Tsaffrir, et al., "Linearization of the Bradford Protein Assay Increases Its Sensitivity: Theoretical and Experimental Studies," 236 Analytical Biochemistry 302–308, Article No. 0171 (1996).

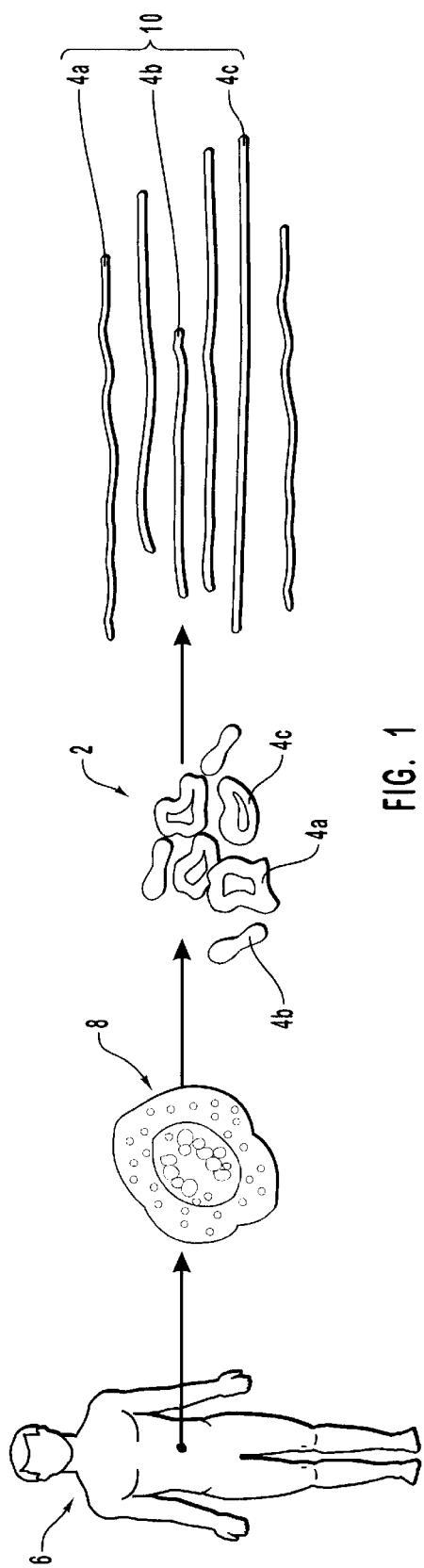
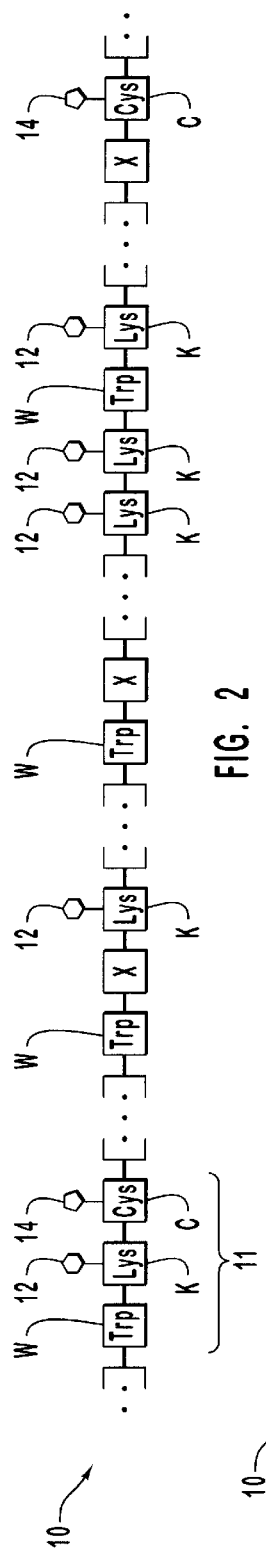
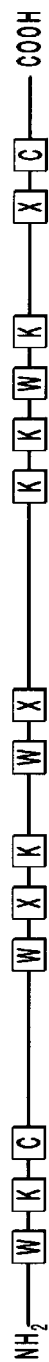
FIG. 1
FIG. 2
FIG. 3
FIG. 4

PROTEIN FINGERPRINT SYSTEM AND RELATED METHODS

BACKGROUND

1. The Field of the Invention

This invention relates to the rapid identification of protein molecules by the systematic development for each respective type of protein molecule of a set of particular, invariant, readily-detectable distinguishing characteristics, which set of characteristics will for convenience hereinafter be referred to as a fingerprint for the corresponding type of protein molecule. The invention also relates to libraries of different protein molecules and the corresponding fingerprints therefor, as well as to systems used in the identification, or fingerprinting, of protein molecules. The present invention has particular applicability to the identification of protein molecules obtained from biological samples.

2. Background Art

There are approximately 100,000 different types of protein molecules involved in organic processes. Each protein molecule is, however, comprised of various amino acid building blocks from a group of about twenty different amino acids. Amino acids chemically connect end-to-end to form a chain that is referred to as a peptide. The amino acid building blocks in a peptide chain share as a group various of the peripheral atomic constituents of each amino acid. As a result, an amino acid in a peptide chain is not in situ a complete amino acid. Therefore, an amino acid in a peptide chain is referred to as an "amino acid residue." A peptide chain becomes a true protein molecule only when the constituent amino acid residues have been connected, when certain amino acid residues of the peptide chain have been modified by the addition to or removal of certain types of molecules from the functional chemical groups of these amino acid residues, and when the completed chain of amino acid residues assumes a particular three-dimensional structure determined by the sequence of amino acid residues and chemical modifications thereof.

Protein molecules do not naturally maintain a one-dimensional, linear arrangement. The sequence of the amino acid residues in a protein molecule causes the molecule to assume an often complex, but characteristic three-dimensional shape. A protein molecule that has been forced out of this three-dimensional shape into a one-dimensional, linear arrangement is described as having been "linearized."

Protein molecules are involved in virtually every biological process. Aberrant or mutant forms of protein molecules disrupt normal biological processes, thereby causing many types of diseases, including some cancers and inherited disorders, such as cystic fibrosis and hemophilia. The ability of a protein molecule to perform its intended function depends, in part, upon the sequence of amino acid residues of the protein molecule, modifications to particular amino acid residues of the protein molecule, and the three-dimensional structure of the protein molecule.

Alterations to the sequence of amino acid residues, to the modifications of particular amino acid residues, or to the three-dimensional structure of a protein molecule can change the way in which a protein molecule participates in biological processes. While many protein molecules and the functions thereof in biological processes are known, scientists continue the arduous task of isolating protein molecules, identifying the chemical composition and structure of each isolated protein molecule, and determining the functions of the protein molecule, as well as the consequences of changes in the structures of the protein molecule.

The sequence of the amino acid residues in a protein molecule, which imparts to the protein molecule a unique identity with a set of unique characteristics, is difficult to detect rapidly and reliably.

The identification of a protein molecule typically involves two steps: (1) purifying the protein molecule; and (2) characterizing the protein molecule.

In isolating or purifying protein molecules, a targeted protein molecule is separated from other, different types of protein molecules. Some current purification techniques are sensitive enough to purify an aberrant form of a protein molecule from normal protein molecules of the same type. Different purification techniques are based on the different characteristics of protein molecules, such as the weight of a protein molecule, the solubility of a protein molecule in water and other solvents, the reactivity of a protein molecule with various reagents, and the pH value at which the protein molecule is electrically neutral. The last is referred to as the isoelectric point of the protein molecule. Due to the large number of different types of protein molecules and because some types of protein molecules have very similar characteristics to other types of protein molecules, extremely sensitive purification processes are often required to isolate one type of protein molecule from others. The sensitivity with which similar types of protein molecules are separated from each other can be enhanced by combining different types of these purification techniques.

In some characterization processes, individual protein molecules are studied. When characterization processes that permit one to study individual protein molecules are employed, a single protein molecule in a sample can be separated or isolated from the other protein molecules in the sample by diluting the sample.

Since many purification techniques separate different types of protein molecules on the bases of the physical or chemical characteristics of the different types of protein molecules, these purification techniques may themselves reveal some information about the identity of a particular type of protein molecule. Once a particular type of protein molecule has been purified, it may be necessary to further characterize the purified protein molecule in order to identify the purified protein molecule. This is particularly true when attempting to characterize previously unidentified types of protein molecules, such as aberrant or mutant forms of a protein molecule.

Typically, protein molecules are further characterized by employing techniques that determine the weight of the protein molecule with increased sensitivity over techniques like gel electrophoresis, or by determining the sequence of amino acid residues that make up the protein molecule. One technique that is useful for performing both of these tasks is mass spectrometry.

In order to characterize a type of protein molecule by mass spectrometry, a purified type of protein molecule or a particular segment of a purified type of protein molecule is given positive and negative charges, or ionized, and made volatile in a mass spectrometer. The ionized, volatilized protein molecules or segments are then analyzed by the mass spectrometer. This produces a mass spectrum of the protein molecule or segment. The mass spectrum provides very precise information about the weight of the protein molecule or segment. Due to the precision with which a mass spectrometer determines the weight of protein molecules and segments of protein molecules, when a protein molecule or segment is analyzed, the information provided by mass spectrometry can be of use in inferring the sequence of amino acid residues in the protein molecule or segment. Mass spectrometers are also sensitive enough to provide information about modifications to particular amino acid residues of a protein molecule or segment. When a series of segments from a certain type of protein molecule are analyzed by mass spectrometry, the information about the sequences of and modifications to the amino acid residues of each segment can be combined to infer the sequence of and modifications to amino acid residues of an entire protein molecule.

Due to the sensitivity of mass spectrometry and the resulting ability to infer the sequences of the amino acid residues and modifications thereto of a particular type of protein molecule, the differences of aberrant or mutant forms of protein molecules from a normal protein molecule in amino acid residue sequences and amino acid residue modifications can also be inferred.

Nonetheless, mass spectrometry is a time-consuming process that requires expensive equipment and reagents.

SUMMARY OF THE INVENTION

It is thus a broad object of the present invention to increase the speed and efficiency with which protein molecules can be characterized.

It is also an object of the present invention to lend to a protein molecule a characteristic set of ancillary properties that are rapidly and reliably detectable.

It is a further object of the present invention to generate a listing of known protein molecules and their corresponding fingerprints as provided and determined by the method of the present invention.

Achieving the foregoing objects will fulfill further, broader objects of the present invention of improving biochemical research and healthcare.

To achieve the foregoing objects, and in accordance with the invention as embodied and broadly described herein, systems and methods for characterizing protein molecules are provided. Also provided are protein molecules having such tags attached thereto as impart the protein molecules distinguishing characteristics that are useable as fingerprints.

In one form, a system incorporating teachings of the present invention, which is capable of characterizing a protein molecule, lends to a protein molecule a characteristic set of ancillary properties that is rapidly and reliably detectable. As these ancillary properties are as uniquely identifying of the type of the protein molecule as fingerprints are reflective of the identity of a human being, the characteristic set of ancillary properties of a protein molecule function as a "fingerprint" of the protein molecule that may be used to rapidly and reliably identify the type of the protein molecule.

A system according to teachings of the present invention has denaturation means for linearizing the protein molecule, labeling means for attaching a tag to each of a first type of amino acid residue of the protein molecule, and detector means for detecting a fingerprint of the tagged protein molecule. The fingerprint of the protein molecule has a first fingerprint constituent imparted to the protein molecule by the tags on each first type of amino acid residue in the protein molecule and a second fingerprint constituent imparted to the protein molecule by each second type of amino acid residue in the protein molecule.

A system according to teachings of the present invention may also include isolation means for separating the protein molecule from other protein molecules in a sample, as well as collation means for comparing the fingerprint of a protein molecule of interest to the fingerprints of known protein molecules listed in a library.

An example of the denaturation means is a detergent, such as sodium dodecyl sulfate (hereinafter "SDS"), which gives the entire protein molecule a negative charge and therefore pulls the protein molecule out of its three-dimensional structure. Another example of the denaturation means is β-mercaptoethanol, a chemical that breaks chemical linkages between the sulfur atoms of two amino acid residues.

A protein molecule of interest is separated from the other types of protein molecules present in a sample by way of isolation means for separating the protein molecule. Examples of isolation means that are useful in the systems and methods of the present invention include, without limitation, hydrodynamic focusing apparatus, electrophoretic gels, separation plates with apertures therethrough, and dilution systems for the sample in which the protein molecule of interest is located.

In a first example of the labeling means, a fluorescent dye is attached chemically to the amino acid residues in a protein molecule of a specific chosen type, thereby forming a tag on each amino acid residue of the specific chosen type in the protein molecule. In a second example, the labeling means is a metallic tag precursor that chemically bonds with the amino acid residues in protein a specific chosen type to form a tag on each amino acid residue of the specific chosen type in the protein molecule.

Of the twenty or so types of amino acid residues in protein molecules, one type of amino acid residue, known as tryptophan, self-fluoresces when exposed to electromagnetic excitation radiation of a certain range of wavelengths.

When a fluorescent dye is used as the labeling means, an example of the detector means includes electromagnetic excitation radiation of one or more excitation wavelengths or a range of excitation wavelengths that will stimulate the tryptophan amino acid residues of a protein molecule to emit radiation of a first emitted wavelength. The excitation radiation of the detector means will also cause the fluorescent dye to emit radiation of a second emitted wavelength. In this example, the detector means also includes a detector that is sensitive to the wavelengths of emitted radiation from the tryptophan amino acid residues of the protein molecule and to the fluorescent dye.

When the tags attached to each of the specific type of amino acid residue of the protein molecule are metallic, the detector means can include a nuclear magnetic resonance apparatus or other apparatus known in the art to be capable of detecting single metal atoms.

Alternatively, tags can be attached to more than one type of amino acid residue of the protein molecule. The tags on one type of amino acid residue are differentially detected from the tags on one or more other types of amino acid residues to determine different fingerprint constituents of the protein molecule.

According to another aspect of the invention, a listing or database is generated for use with specific protocols to identify protein molecules. This listing or database is referred to herein as a library, and includes the identities of a set of known protein molecules and information about the different fingerprint constituents of each of the known protein molecules of the listing. The different fingerprint constituents are imparted to the protein molecule by the labeling means of the system and detected by way of the detection means of the system. Collation means for comparing the fingerprint of a protein molecule of interest to the fingerprints of the known protein molecules listed in the library are then used to identify the protein molecule of interest. Typically, the function of such a collation means can be performed by a computer processor.

In yet another aspect, the present invention includes protein molecules that have been labeled with tags to impart fingerprint constituents to the protein molecule. Each fingerprint constituent indicates the number of a particular type of amino acid residue in a protein molecule and the relative locations of different types of amino acid residues in the protein molecule.

The prospect of being able to rapidly and reliably identify a type of protein molecule has utility in a wide range of research and clinical applications, such as, for example, in determining whether or not selected cells of a patient have entered early stages of cancer.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

A more particular description of the invention briefly described above will be rendered by reference to a specific embodiment thereof which is illustrated in the appended drawings in order to illustrate and describe the manner in which the above-recited and other advantages and objects of the invention are obtained. Understanding that these drawings depict only a typical embodiment of the invention and are not therefore to be considered limiting of its scope, the invention will be described and explained with additional specificity and detail through the use of the accompanying drawings in which:

FIG. 1 schematically illustrates steps by which a mixed sample of different types of proteins might routinely be obtained;

FIG. 2 is a schematic diagram of a portion of a sequence of amino acid residues in a typical protein molecule with selected of those amino acid residues tagged;

FIG. 3 is a schematic diagram of the portion of the protein molecule of FIG. 2 with selected of the amino acid residues therein, including the tagged amino acid residues, symbolized in simplified form at a higher level of abstraction;

FIG. 4 is a schematic illustration of the portion of the protein molecule illustrated in FIG. 3 symbolized with yet enhanced simplicity at an even higher enhanced level of abstraction;

DETAILED DESCRIPTION OF THE ILLUSTRATED EMBODIMENTS

Figure 5:
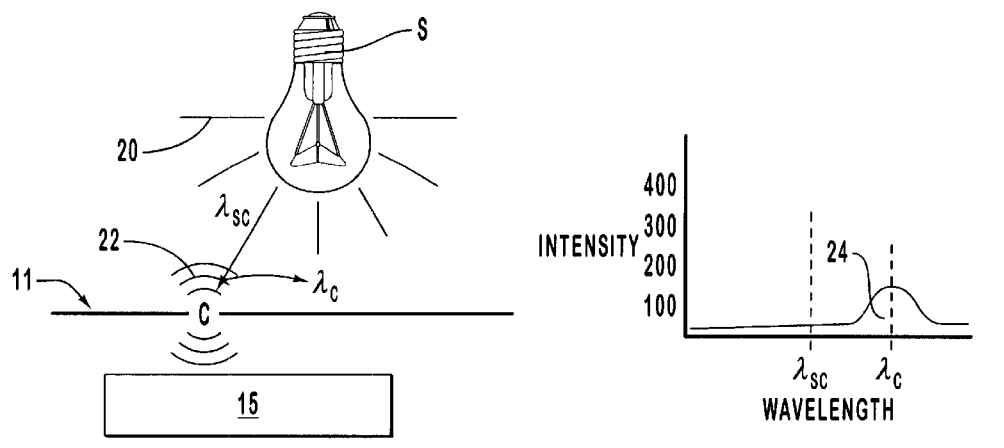
FIG. 5 is a schematic illustration of a method incorporating teachings of the present invention for obtaining a first fingerprint constituent for a segment of the protein molecule depicted in FIG. 4 using a single-stage emission produced by exposing the segment to electromagnetic radiation at a first excitation wavelength.

FIG. 1 depicts steps by which a mixed sample 2 of different types of protein molecules 4a, 4b, 4c might routinely be obtained from a living organism 6, such as an animal, a plant, a microorganism, or the human being depicted. A biological sample 8, such as tissue or the illustrated cell, is secured from living organism 6. Mixed sample 2 of protein molecules 4a, 4b, 4c is then obtained from biological sample 8 by, for example, disrupting the cell membranes. Protein molecules 4a, 4b, 4c are then linearized from three-dimensional structures to one-dimensional structures, such as the linearized protein molecules 10 depicted to the right in FIG. 1.

FIG. 2 illustrates a single linearized protein molecule 10. Protein molecule 10 is a chain of amino acid residues that includes a number of amino acid residues K of a first type, a number of amino acid residues C of a second type, a number of tryptophan amino acid residues W, and a number of amino acid residues X of other types, many of which are not shown, but only suggested by ellipsis. A first type of tag 12 is shown chemically attached to each amino acid residue K of protein molecule 10. A second type of tag 14 is shown chemically attached to each amino acid residue C. In FIG. 2 no such tags are attached to tryptophan amino acid residues W or to other amino acid residues X. Tags 12 and 14 may be different types of fluorescent tags, different types of metallic tags, or different types of tags of some other detectable genre.

A subcombination of adjacently connected amino acid residues in protein molecule 10 is identified in FIG. 2 as peptide 11. In left-to-right sequence, a single amino acid residue W, and amino acid residue K carrying a tag 12, in an amino acid residue C carrying a tag 14. As illustrated, amino acid residue W is tryptophan, amino acid residue K is lysine, and amino acid residue C is cysteine.

Protein molecule 10 of FIG. 2 is again depicted in FIG. 3 with selected of the amino acid residues therein, including amino acid residues W, K, and C, symbolized in simplified form at a higher level of abstraction. $NH_2$ represents a first end, or terminus, of protein molecule 10 and COOH represents a second end of protein molecule 10.

FIG. 4 illustrates protein molecule 10 symbolized with yet enhanced simplicity at an even higher enhanced level of abstraction relative to that of FIGS. 2 and 3.

According to one aspect of the teachings of the present invention, FIGS. 5–7C illustrate a method for characterizing a protein molecule on the basis of ancillary properties imparted to the protein molecule by the natural fluorescence of tryptophan amino acid residues and by fluorescent tags attached to substantially all of the lysine and cysteine amino acid residues of the protein molecule.

For convenience in illustrating the implementation of the disclosed protein fingerprinting technology, peptide 11 is illustrated, apart from the balance of protein molecule 10, as a straight line in. FIGS. 5–7C. In the depictions of peptide 11 in these figures, only the amino acid residue W, K, or C of immediate concern to the corresponding discussion will be illustrated. As a further simplification, tag 12 on amino acid residue K and tag 14 on amino acid residue C have been omitted, as was the case in FIGS. 3 and 4. Nonetheless, the depictions in these figures are illustrative only, and tag 12 and tag 14 should be understood to be present, respectively, on amino acid residue K and amino acid residue C.

For illustrative purposes, tag 12 and tag 14 are tags that fluoresce when exposed to an appropriate respective wavelength of electromagnetic radiation. Tryptophan amino acid residue W is naturally flourescent, meaning that amino acid residue W will fluoresce when exposed to an appropriate wavelength of electromagnetic radiation, even without the attachment thereto of any flourescent tag, such as tag 12 or tag 14. Therefore, no such flourescent tag is shown on amino acid residues W in FIG. 2 or is to be suggested in the other of the accompanying figures.

FIG. 5 illustrates peptide 11 of protein molecule 10 exposed to a source S of a First primary electromagnetic excitation radiation 20 of wavelength $\lambda_{SC}$. First primary electromagnetic excitation radiation 20 stimulates the tag on amino acid residue C to fluoresce, producing emitted radiation 22 of wavelength $\lambda_C$.

The intensity of emitted radiation 22 is measured by a detector 15 and subjected to a spectral analysis that is reflected in the graph to the right in FIG. 5. That graph is characterized by a peak centered about wavelength $\lambda_C$ that serves as a fingerprint constituent 24 for peptide 11 at wavelength $\lambda_{SC}$.

Thus, as illustrated in the spectral diagram of FIG. 5, when a flourescent tag is chemically attached to amino acid residue C, first primary electromagnetic excitation radiation 20 of wavelength $\lambda_{SC}$ stimulates the emission of a corresponding fingerprint constituent 24. Nonetheless, the activity reflected in FIG. 5 is but a depiction of activity related to a single amino acid residue C in isolation from all other amino acid residues in peptide 11 or even in protein molecule 10.

Different approaches are used to obtain a corresponding fingerprint constituent for the entirety of protein molecule 10 at wavelength $\lambda_{SC}$.

In a relatively global approach, first primary electromagnetic excitation radiation 20 is used to illuminate the entire length of protein molecule 10. The cumulative intensity of all consequently emitted radiation is measured by a detector and subjected to an appropriate spectral analysis.

Alternatively, linearized protein molecule 10 is scrolled past source S and detector 15. This results in a sequenced series of fingerprint constituents for protein molecule 10 at wavelength $\lambda_{SC}$. This scrolling process produces markedly greater information about the structure of protein molecule 10 than does the global method described previously.

Figure 6A:
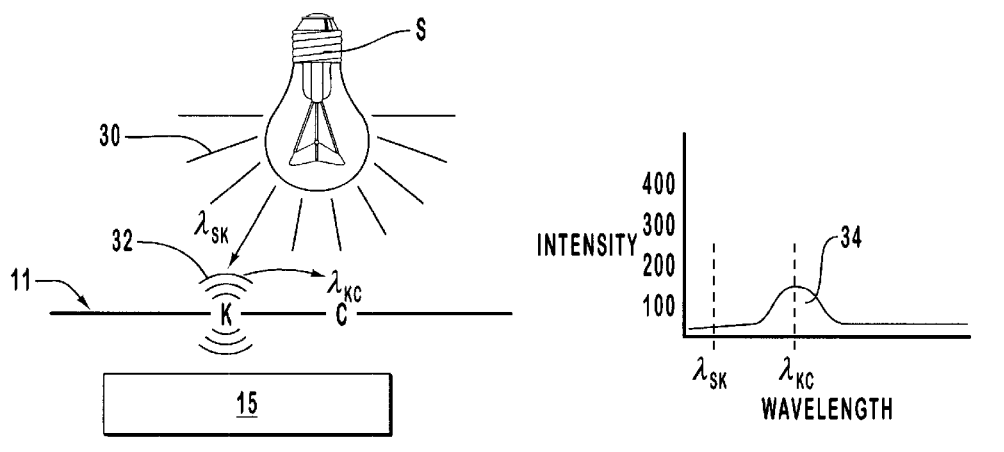
FIGS. 6A and 6B taken together illustrate schematically a method for obtaining a second fingerprint constituent and a third fingerprint constituent for the segment of the protein molecule depicted in FIG. 4 using a two-stage emission produced by exposing the segment to electromagnetic radiation at a second excitation wavelength, FIG. 6A illustrating the initial single-stage emission in the process, and FIG. 6B illustrating the entirety of the two-stage emission initiated thereby.
Figure 6B:
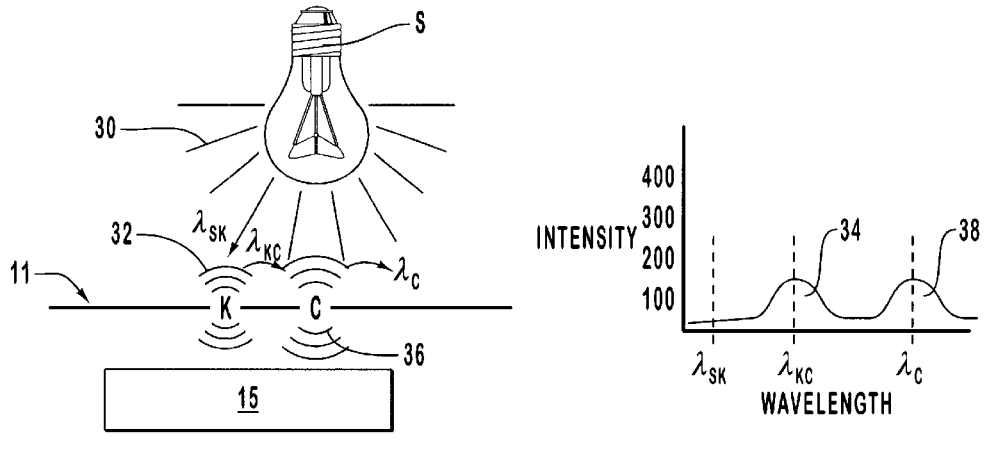

FIGS. 6A and 6B depict in stages the consequence of the exposure of peptide 11 of protein molecule 10 to a source S of a second primary electromagnetic excitation radiation 30 at a wavelength $\lambda_{SK}$ that stimulates the tag on amino acid residue K to fluoresce. The process also stimulates the tag on amino acid residue C to fluoresce, albeit indirectly. Each of FIGS. 6A and 6B includes a graph that depicts a corresponding portion of the response spectra for peptide 11 at wavelength $\lambda_{SK}$.

FIG. 6A illustrates peptide 11 of protein molecule 10 exposed to a source S of a second primary electromagnetic excitation radiation 30 of wavelength $\lambda_{SK}$. Second primary excitation radiation 30 causes the tag on amino acid residue K to fluoresce, producing emitted radiation 32 of wavelength $\lambda_{KC}$.

The intensity of emitted radiation 32 is measured by detector 15 and subjected to a spectral analysis that produces the graph to the right in FIG. 6A. That graph is characterized by a peak centered about wavelength $\lambda_{KC}$. This serves as a first fingerprint constituent 34 for peptide 11 at wavelength $\lambda_{KC}$.

Emitted radiation 32 is, however, capable of exciting the tag on amino acid residue C to fluoresce.

FIG. 6B illustrates that the exposure of peptide 11 to emitted radiation 32 excites the tag on amino acid residue C. This causes the tag on amino acid residue C to fluoresce, producing emitted radiation 36 of wavelength $\lambda_C$.

The intensity of emitted radiation 32 and the intensity of emitted radiation 36 are measured by detector 15 and subjected to a spectral analysis that produces the graph to the right in FIG. 6B. That graph is characterized not only by first fingerprint constituent 34, but by a second peak centered about wavelength $\lambda_C$. The latter serves as a second fingerprint constituent 38 for peptide 11 at wavelength $\lambda_{SK}$.

For emitted radiation 32 to have the illustrated effect on the tag on amino acid residue C, the tag on amino acid residue K that produced emitted radiation 32 must be located relatively proximately along protein molecule 10 to the tag on amino acid residue C.

Thus, as illustrated in the spectral diagram of FIG. 6B, when flourescent tags are chemically attached to two different types of amino acid residues K and C, second primary electromagnetic excitation radiation 30 of wavelength $\lambda_{SK}$ that excites the tag on amino acid residue K will stimulate the emission of two corresponding additional fingerprint constituents for peptide 11.

Figure 7A:
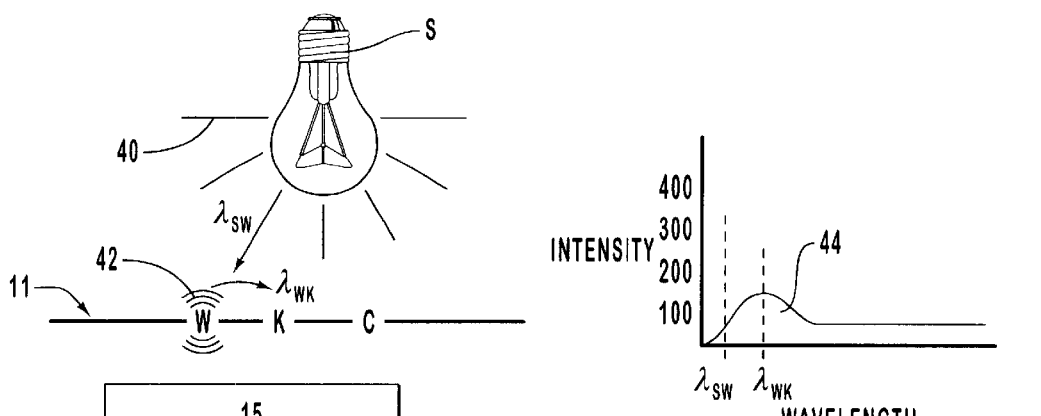
FIGS. 7A–7C taken together illustrate schematically a method for obtaining fourth, fifth, and sixth fingerprint constituents for the segment of the protein molecule depicted in FIG. 4 using a three-stage emission produced by exposing the segment to electromagnetic radiation at a third excitation wavelength, FIG. 7A illustrating the initial single-stage emission, FIG. 7B illustrating the two-stage emission caused thereby, and FIG. 7C illustrating the entirety of the three-stage emission.
Figure 7B:
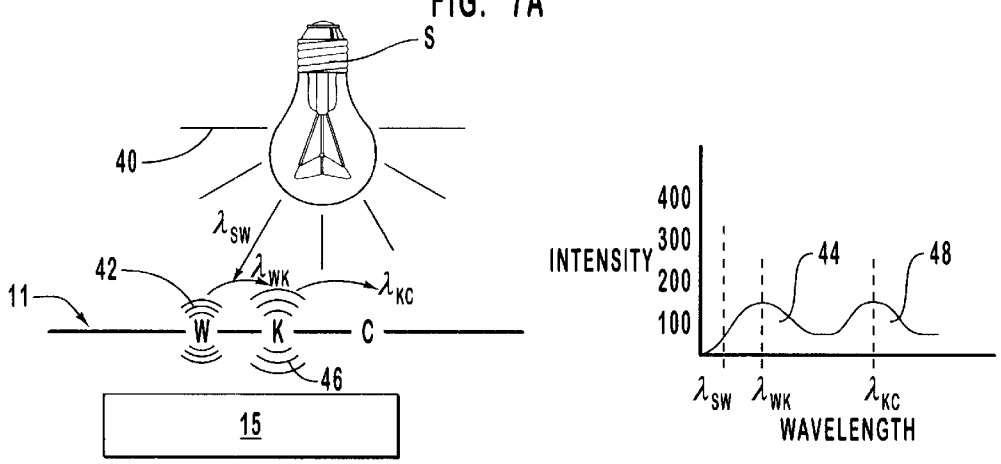
Figure 7C:
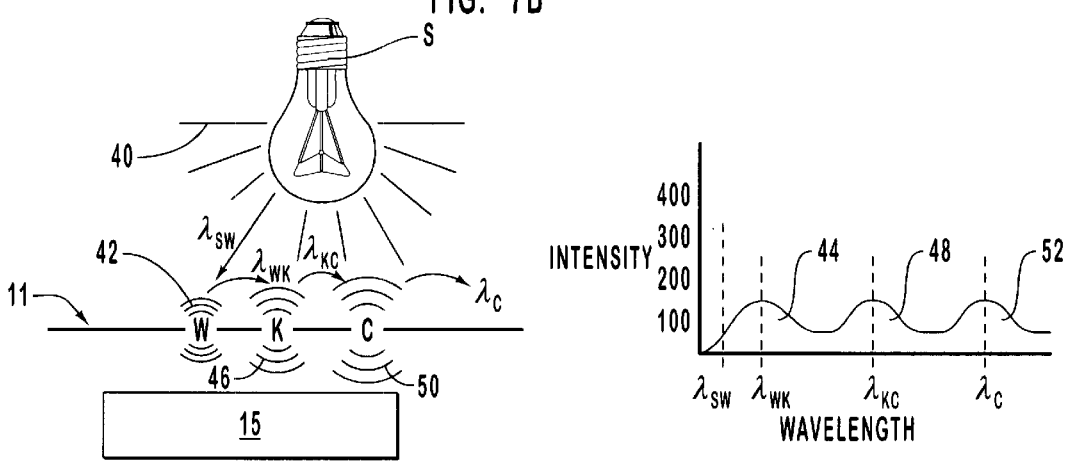

FIGS. 7A–7C illustrate in stages the consequence of the exposure of peptide 11 of protein molecule 10 to a source S of a third primary electromagnetic excitation radiation 40 at a wavelength $\lambda_{SW}$ that stimulates tryptophan amino acid residue W to fluoresce. The process also indirectly stimulates the tags on amino acid residues K and C of peptide 11 to fluoresce. Each of FIGS. 7A–7C includes a graph that depicts a corresponding portion of the response spectra for peptide 11 at wavelength $\lambda_{SW}$.

In FIG. 7A it can be seen that the exposure of peptide 11 to third primary electromagnetic excitation radiation 40 excites tryptophan amino acid residue W. This causes tryptophan amino acid residue W to fluoresce, producing emitted radiation 42 of wavelength $\lambda_{WK}$. The intensity of emitted radiation 42 is measured by detector 15 and subjected to a spectral analysis that produces the graph to the right in FIG. 7A. That graph is characterized by a peak centered about wavelength $\lambda_{WK}$ that serves as a first fingerprint constituent 44 for peptide 11 at wavelength $\lambda_{SW}$.

Emitted radiation 42 of FIG. 7A is, however, radiation that is capable of exciting the tag on amino acid residue K to fluoresce.

In FIG. 7B it can be seen that the exposure of peptide 11 to emitted radiation 42 excites the tag on amino acid residue K. This causes the tag on amino acid residue K to fluoresce, producing emitted radiation 46 of wavelength $\lambda_{KC}$. The intensity of emitted radiation 46 is measured by detector 15 and subjected to a spectral analysis that produces the graph to the right in FIG. 7B. That graph is characterized, not only by first fingerprint constituent 44, but by a second peak centered about wavelength $\lambda_{KC}$. The latter serves as a second fingerprint constituent 48 for peptide 11 at wavelength $\lambda_{SW}$.

For emitted radiation 42 to have the illustrated effect on the tag on amino acid residue K, tryptophan amino acid residue W that produced emitted radiation 42 must be located relatively proximately along protein molecule 10 to the tag on amino acid residue K.

Emitted radiation 46 of FIG. 7B is, however, radiation that is capable of exciting the tag on amino acid residue C to fluoresce.

In FIG. 7C it can be seen that the exposure of peptide 11 to emitted radiation 46 excites the tag on amino acid residue C. This causes the tag on amino acid residue C to fluoresce, producing emitted radiation 50 of wavelength $\lambda_C$. The intensity of emitted radiation 50 is measured by detector 15 and subjected to a spectral analysis that produces the graph to the right in FIG. 7C. That graph is characterized not only by first fingerprint constituent 44 and second fingerprint constituent 48, but by a third peak centered about wavelength $\lambda_C$. The latter serves as a third fingerprint constituent 52 for peptide 11 at wavelength $\lambda_{SW}$.

For emitted radiation 46 to have the illustrated effect on the tag on amino acid residue C, the tag on amino acid residue K that produced emitted radiation 46 must be located relatively proximately along protein molecule 10 to the tag on amino acid residue C.

Thus, as illustrated in the spectral diagram of FIG. 7C, when fluorescent tags are chemically attached on two different types of amino acid residues K and C, third primary electromagnetic excitation radiation 40 of wavelength $\lambda_{SW}$ that excites tryptophan amino acid residue W will stimulate the emission of three corresponding fingerprint constituents for peptide 11 at wavelength $\lambda_{SW}$.

Fingerprint constituents 24, 34, 38, 44, 48, and 52 together comprise one possible fingerprint for peptide 11, or by comparison for protein molecule 10. Fingerprint constituents are obtained for additional known protein molecules and collected in a computer database. The database then serves as a library of fingerprints for a set of protein molecules with tags on amino acid residues K, C when exposed to primary excitation radiations of wavelengths $\lambda_{SC}$, $\lambda_{SK}$, and $\lambda_{SW}$.

An unknown protein molecule is identified by chemically attaching the same types of tags to all corresponding types of amino acid residues of that protein molecule. Fingerprint constituents of the unknown protein molecule are determined using the methodology described. The fingerprint constituents of the unknown protein molecule are compared to the entries in the library of protein fingerprints. If a matching set of protein fingerprints is located in the library, the unknown protein molecule is identified.

The disclosed fingerprinting method can be used to rapidly identify a plurality of unknown protein molecules in a mixture of protein molecules, such as those contained within a sample cell.

Figure 8:
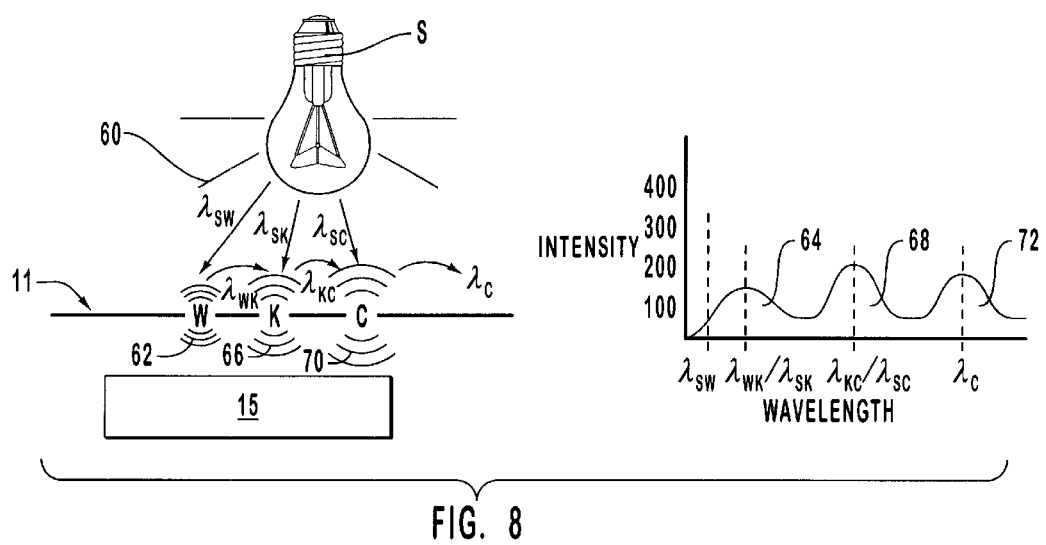
FIG. 8 is a schematic illustration of a second embodiment of a method incorporating teachings of the present invention for obtaining three fingerprint constituents for a segment of the protein molecule depicted in FIG. 4 using a three-stage emission produced by exposing the segment to electromagnetic radiation of a broad range of excitation wavelengths.

In a variation of the fingerprinting method illustrated in FIGS. 4–7C, shown in FIG. 8, a single source S that emits a broad spectrum of wavelengths of primary electromagnetic excitation radiation 60, including wavelengths $\lambda_{SW}$, $\lambda_{SK}$, and $\lambda_{SC}$, is used to simultaneously stimulate amino acid residues W, K, and C of peptide 11 to fluoresce.

The process also indirectly stimulates the tags on amino acid residues K and C of peptide 11 to fluoresce. FIG. 8 includes a graph that depicts a corresponding portion of the response spectra for peptide 11 at wavelengths $\lambda_{SW}$, $\lambda_{SK}$, and $\lambda_{SC}$.

In FIG. 8 it can be seen that the exposure of peptide 11 to primary electromagnetic excitation radiation 60 excites tryptophan amino acid residue W. This causes tryptophan amino acid residue W to fluoresce, producing emitted radiation 62 of wavelength $\lambda_{WK}$.

Emitted radiation 62 is radiation that is capable of exciting the tag on amino acid residue K to fluoresce. In addition, wavelength $\lambda_{SK}$ of primary electromagnetic excitation radiation 60 from source S causes the tag on amino acid residue K to fluoresce. When stimulated either by primary electromagnetic excitation radiation 60 or by emitted radiation 62, the tag on amino acid residue K produces emitted radiation 66 of wavelength $\lambda_{KC}$.

Emitted radiation 66 is capable of exciting the tag on amino acid residue C to fluoresce. In addition, wavelength $\lambda_{SC}$ of primary electromagnetic excitation radiation 60 from source S causes the tag on amino acid residue C to fluoresce. When stimulated either by primary electromagnetic excitation radiation 60 or by emitted radiation 66, the tag on amino acid residue C produces emitted radiation 70 of wavelength $\lambda_{C}$.

The intensities of emitted radiation 62, 66, 70 are measured by detector 15 and subjected to a spectral analysis that produces the graph to the right in FIG. 8. That graph is characterized by a first peak centered about wavelength $\lambda_{WK}/\lambda_{SK}$ that serves as a first fingerprint constituent 64 for peptide 11, by a second peak centered about wavelength $\lambda_{KC}/\lambda_{SC}$ that serves as a second fingerprint constituent 68 for peptide 11, and by a third peak centered about wavelength $\lambda_{C}$ that serves as a first fingerprint constituent 72 for peptide 11 when peptide 11 is exposed to primary electromagnetic excitation radiation 60 that includes wavelengths $\lambda_{SW}$, $\lambda_{SK}$, and $\lambda_{SC}$.

Figures 9, 10:
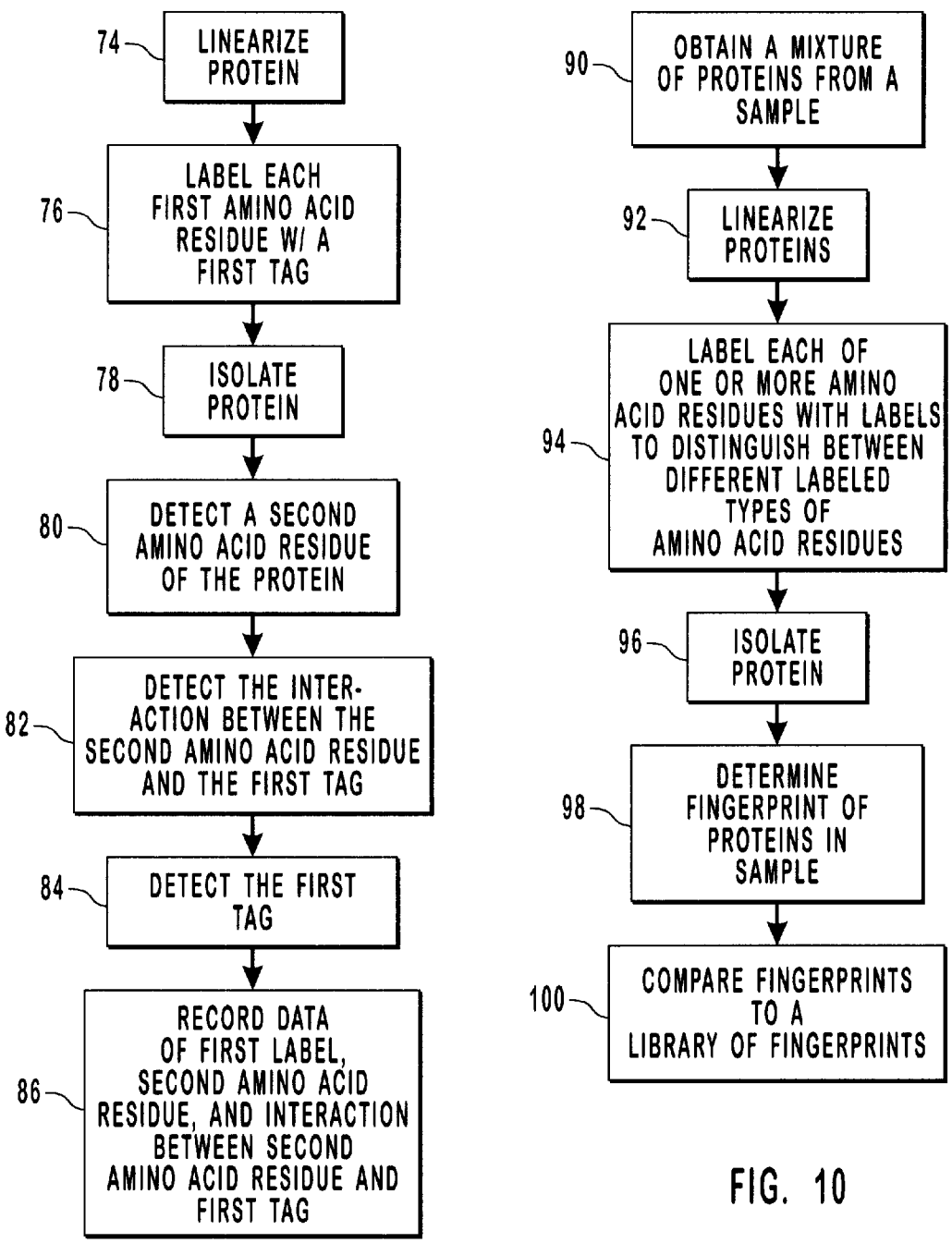
FIG. 9 is a flow chart depicting steps in a method incorporating teachings of the present invention for determining a fingerprint for a protein molecule.
FIG. 10 is a flow chart depicting steps in a method incorporating teachings of the present invention for identifying a protein molecule using a fingerprint thereof determined according to the method of FIG. 9.

In another aspect of the present invention, the characterization of a protein molecule in a manner that incorporates teachings of the present invention is but a step in a method in which proteins are isolated and characterized. FIG. 9 is a flow chart that illustrates, by way of example and not by way of limitation, one such method. The characterization steps of FIG. 9 are broader than the characterization steps illustrated in FIGS. 5–8. Each of the boxes of the flow chart of FIG. 9 represents a general step of the method. The order of the boxes is not intended to be limiting, neither is any single step illustrated, as some of the steps are optional.

In box 74, the protein molecules in a sample are exposed to one or more chemicals to convert the protein molecules from native three-dimensional structures to linear, one-dimensional structures. These chemicals are referred to herein as denaturation means for linearizing the protein molecule. When the structure of a protein molecule has been modified in this manner, the protein molecule is said to have been "linearized."

By way of example and not limitation, linearization means according to the invention can include the use of chemicals that are known to be useful in linearizing a protein molecule. These could include, without limiting the scope of the invention, ionic detergents, such as SDS, and nondetergents, such as the chaotropic salts guanadinium and urea. The chemical known as β-mercaptoethanol, which breaks chemical bonds that can form between sulfur atoms of two amino acid residues, such as methionine and cysteine amino acid residues, can also be used as linearization means.

Alternatively, it may be desirable to analyze a protein molecule in the native three-dimensional structure thereof or without disrupting chemical bonds between sulfur atoms of two amino acid residues.

In box 76, each of a first type of amino acid residue of the protein molecule is labeled with a first tag. The amino acid residues are labeled with tags, such as fluorescent tags or metallic tags. Specific tags can be attached to specific amino acid residues by way of known chemical reactions. Alternatively, the first type of amino acid residues of the protein molecule can be labeled prior to the linearization step depicted in box 74.

In box 78, the protein molecule or type of protein molecule to be examined is isolated from the other protein molecules or types of protein molecules in the sample. The isolation step depicted in box 78 can occur before or after the linearization step depicted in box 74, or before or after the labeling step depicted in box 76.

Once the protein molecule or type of protein molecule to be examined is isolated, the protein molecule can be characterized. In box 80, a second type of amino acid residue of the protein molecule is detected. The second type of amino acid residue can itself be detected, or some signal generated by the second type of amino acid residue can be detected. When fluorescent dyes are employed as the tags on amino acid residues of the first type, the radiation generated due to the self-fluorescence of amino acid residue W when excited by radiation, such as radiation of wavelength $\lambda_{SW}$, is detected, using, for example, the methods illustrated in FIGS. 7A and 8.

Next, in box 82, an interaction between the second type of amino acid residue and the first tag on the first type of amino acid residue is detected. For example, when the first tag is a fluorescent tag as illustrated in FIGS. 7B and 8, the second type of amino acid residue, in this example amino acid residue W, emits radiation of a wavelength $\lambda_{WK}$, which can excite the first tag on the first type of amino acid residue, in this example amino acid residue K.

The first tag on the first type of amino acid residue of the protein molecule is then detected, as depicted by box 84 of the flow chart of FIG. 9. When the first tag is a fluorescent tag, the first tag can be detected by the methods illustrated in FIGS. 6A and 8, wherein peptide 11 is exposed to excitation radiation having a wavelength $\lambda_{SK}$ that will stimulate the first tag to emit detectable radiation.

In box 86, the data obtained from each of the steps depicted by boxes 80, 82, and 84 is recorded. Data can be recorded in any manner known in the art, such as manually or in a computer database.

According to another aspect, the present invention includes a method for identifying an unknown protein molecule. FIG. 10 is a flow chart that depicts exemplary steps that may be carried out to perform the method. Each of the boxes of the flow chart of FIG. 10 represents a general step of the method. The order in which the boxes are presented in FIG. 10 is not meant to be limiting. Moreover, not all of the steps are required in performing the method.

In box 90, a mixture of protein molecules is obtained from a sample. Referring again to FIG. 1, biological sample 8 can be obtained from living organism 6 by known processes. Protein molecules 4a, 4b, 4c can then be removed from biological sample 8 by extraction processes that are known to those in the art.

In box 92 of FIG. 10, the protein molecules obtained from a biological sample are linearized in the same manner as described in reference to box 74 of FIG. 9. The linearization step of box 92 is optional, as it may be desirable to leave the protein molecule completely or partially in the natural three-dimensional configuration thereof.

One or more of the types of amino acid residues of the protein molecule are labeled at box 94. The amino acid residues are labeled with known tags, such as fluorescent tags or metallic tags. Specific tags can be attached to specific amino acid residues by way of known chemical reactions. Accordingly, different fluorescent dyes can be attached to different types of amino acid residues. Alternatively or in addition, one or more of the types of amino acid residues of a protein molecule can be labeled with metallic tags.

As an example, FIG. 2 illustrates each amino acid residue K as having attached thereto a first tag 12. Each amino acid residue C shown in FIG. 2 has a second tag 14 thereon. When different tags are used on different types of amino acid residues, the numbers and relative locations of each of the different types of amino acid residues can be distinguished from each other. FIGS. 5–8 illustrate an example of how different tags on different types of amino acid residues are used to characterize a protein molecule.

Figure 11:
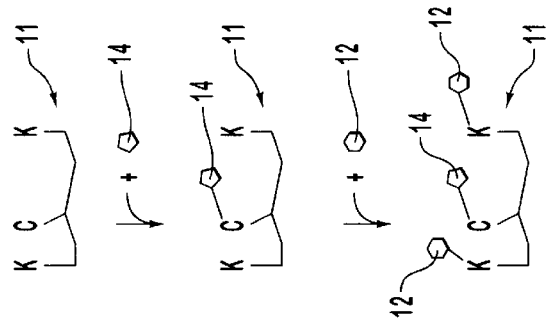
FIG. 11 is a schematic diagram of steps in a first embodiment of a method for labeling more than one type of amino acid residue of a protein molecule with tags.

Different types of amino acid residues in protein molecules are labeled using various methods. A first embodiment of such a method is shown in FIG. 11 by way of illustration and not limitation. A cysteine reactive fluorescent tag 14 is attached to each amino acid residue C of peptide 11 by known processes. A different, lysine reactive fluorescent tag 12 is attached to each amino acid residue K of peptide 11, also by known processes.

Figure 12:
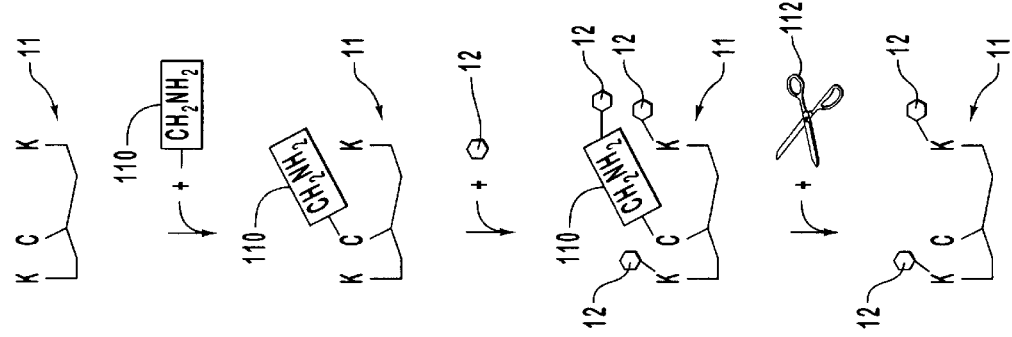
FIG. 12 is a schematic diagram illustrating steps in a second embodiment of a method for labeling more than one type of amino acid residue of a protein molecule with tags and intermediate structures.

FIG. 12 depicts, by way of illustration and not limitation, a second embodiment of labeling method conducted according to the teachings of the present invention. In the second embodiment, a cysteine reactive amino group 110 having the chemical formula $-CH_2NH_2$ is attached to each amino acid residue C of peptide 11. Cysteine reactive amino group 110 permits lysine reactive groups to be attached to amino acid residue C. A lysine reactive fluorescent tag 12 is then attached to each amino acid residue K and to cysteine reactive amino group 110 on each amino acid residue C of peptide 11. The emitted radiation from tags 12 is detected to provide a first fingerprint constituent of peptide 11. After the emitted radiation of tag 12 is detected, tags 12 attached to cysteine reactive amino groups 110 on amino acid residues C can be removed by use of a hydrolyzing reagent 112, as known in the art. Tags 12 remaining only on amino acid residues K can then be detected to provide a second fingerprint constituent of peptide 11.

Figure 13:
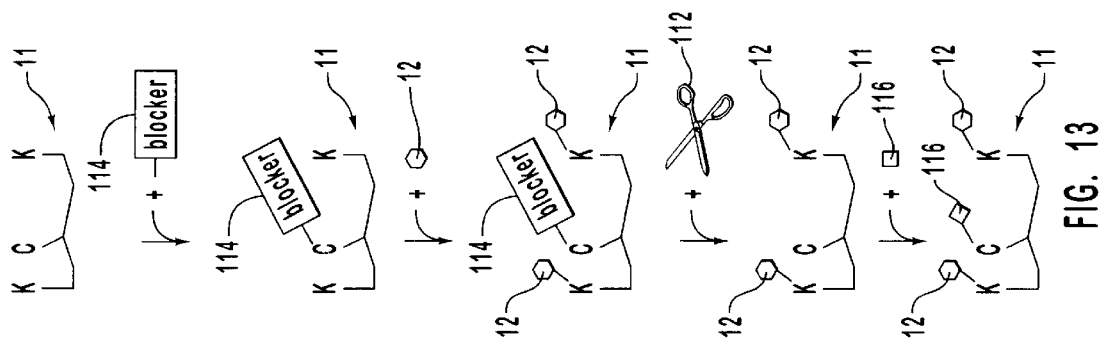
FIG. 13 is a schematic diagram depicting steps in a third embodiment of a method for labeling more than one type of amino acid residue of a protein molecule with tags and intermediate structures.

A third embodiment of labeling method according to teachings of the present invention is shown in FIG. 13 by way of illustration and not limitation. First, a cysteine reactive blocking group 114 of a type known in the art is chemically attached to each amino acid residue C of peptide 11. A lysine reactive fluorescent tag 12 is then attached to each amino acid residue K of peptide 11. Blocking group 114 is then removed from each amino acid residue C by use of a hydrolyzing reagent 112, as known in the art. Next, a different fluorescent tag 116 that can react with either amino acid residue K or amino acid residue C is then chemically attached to each amino acid residue C.

Returning to the inventive method illustrated in FIG. 10, box 96 depicts the isolation of a protein molecule from other protein molecules in the sample, or of a type of protein molecule from other types of protein molecules in the sample. The isolation of a protein molecule from other protein molecules or of a type of protein molecule from other types of protein molecules can occur before or after the linearization step depicted in box 92, or before or after the labeling step depicted in box 94.

Once the desired protein molecule or type of protein molecule has been isolated, the protein molecule or type of protein molecule is characterized at box 98. In characterizing a protein molecule or type of protein molecule, a fingerprint of the protein molecule is determined. FIGS. 5–7B and 8 illustrate examples of a method for determining the fingerprint of a protein molecule, in which amino acid residues of the protein molecule are labeled with fluorescent tags.

When the fingerprint of a protein molecule of interest has been determined, that fingerprint is compared at box 100 to the fingerprints in a library of fingerprints. The library of fingerprints has a listing of known protein molecules. Each of the known protein molecules in the listing has a corresponding fingerprint that was determined by the same processes used to determine the fingerprint of the protein molecule of interest. Thus, when the fingerprint of the protein molecule of interest matches with a fingerprint in the library, the protein molecule of interest is identified.

Figure 14:
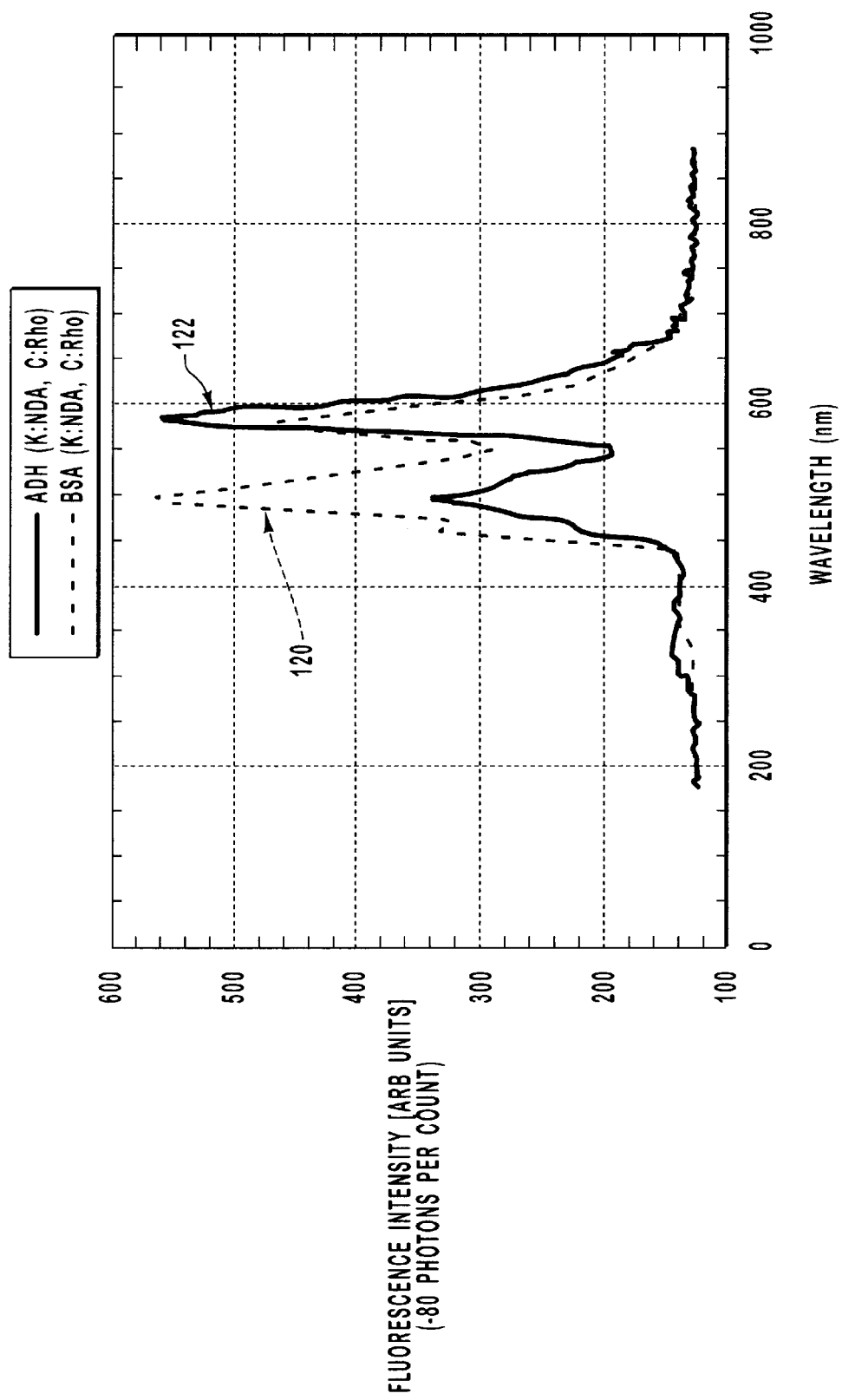
FIG. 14 is a graph depicting fingerprints imparted to two different types of protein molecules by attaching two different fluorescent tags to each of two different types of amino acid residues of the protein molecules.

FIG. 14 is a graph that illustrates the fluorescence spectra, or fingerprints 120, 122, of two different protein molecules. Fingerprints 120, 122 were obtained by the method illustrated in FIG. 8. Fingerprint 120 is characteristic of the protein molecule known as bovine serum albumin (hereinafter "BSA"), while fingerprint 122 corresponds to the protein molecule known as alcohol dehydrogenase (hereinafter "ADH"). Each of fingerprints 120, 122 includes a pair of major intensity peaks, respectively at the same wavelengths.

Fingerprints 120, 122 are imparted to BSA and to ADH by way of the self-fluorescence of each of the tryptophan amino acid residues, the fluorescence of napthalenedicarboxyaldehyde (hereinafter "NDA") tags on each of the lysine amino acid residues, and the fluorescence of rhodamine tags on each of the cysteine amino acid residues of BSA and of ADH.

The present invention includes various approaches to isolating a protein molecule of interest and to determining a fingerprint of the protein molecule of interest. Structures capable of performing each of these functions are respectively referred to as isolation means for separating the protein molecule and detector means for detecting the fingerprint of the protein molecule. FIGS. 15–33 illustrate, by way of example and not limitation, various combinations of structures for performing the functions of an isolation means and a detector means according to teachings of the present invention, thereby to isolate and determine a fingerprint of a protein molecule of interest.

Figure 15:
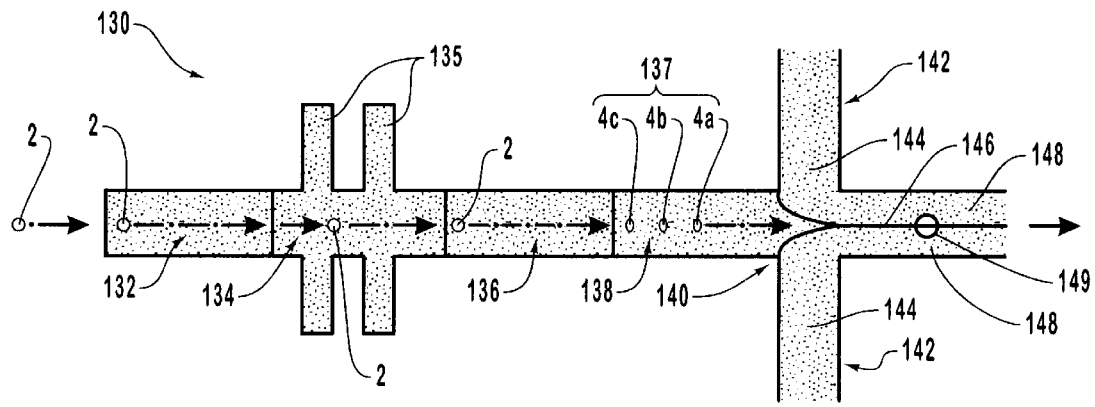
FIG. 15 is a schematic representation of a first embodiment of an apparatus used according to teachings of the present invention to isolate a protein molecule from other protein molecules in a sample for the purpose of facilitating the determination of a fingerprint therefor.

FIG. 15 illustrates a first embodiment of detector means that can be used according to teachings of the present invention to isolate a protein molecule from other protein molecules in a sample for the purpose of characterizing or identifying the protein molecule. The apparatus depicted in FIG. 15 is a hydrodynamic focusing apparatus 130 that isolates individual protein molecules from each other.

Hydrodynamic focusing apparatus 130 has a first region 132 into which sample 2 of one or more protein molecules is introduced. From first region 132, sample 2 flows into a second region 134 of hydrodynamic focusing apparatus 130, where the protein molecules in sample 2 are linearized and labeled with tags by way of chemicals introduced into second region 134 by way of inlets 135. Next, sample 2 flows into a third region 136, where the different types of protein molecules in sample 2 are separated from each other. Third region 136 can have therein a small separation column, a microelectrophoresis gel, or other apparatus known to be capable of separating different types of protein molecules. An eluent 137 that includes the different types of protein molecules 4a, 4b, 4c from sample 2 flows from the separation apparatus of third region 136 into a fourth region 138 of hydrodynamic focusing apparatus 130. Different types of protein molecules 4a, 4b, 4c elute separately from the separation apparatus of third region 136 into fourth region 138.

Eluent 137, which contains separated types of protein molecules 4a, 4b, 4c, flows through fourth region 138, into a laminar flow region 140 of hydrodynamic focusing apparatus 130. Two opposing inlets 142 communicate with laminar flow region 140 to permit the introduction of a buffer 144 into laminar flow region 140. Buffer 144 is introduced under pressure to create a laminar flow of buffer 144 and eluent 137 as the flow paths of eluent 137 and buffer 144 merge. Due to the laminar flow of buffer 144 into eluent 137, eluent 137 flows in a thin layer 146 between two layers 148 of buffer 144. When buffer 144 is introduced into laminar flow region 140 under sufficient pressure, individual protein molecules 4a, 4b, 4c are isolated by the laminar flow of buffer 144 into eluent 137.

As protein molecules 4a, 4b, 4c flow in thin layer 146 through a detection region 149 of hydrodynamic focusing apparatus 130, a fingerprint can be determined that is imparted to each of protein molecules 4a, 4b, 4c in accordance with teachings of the present invention.

Figure 16:
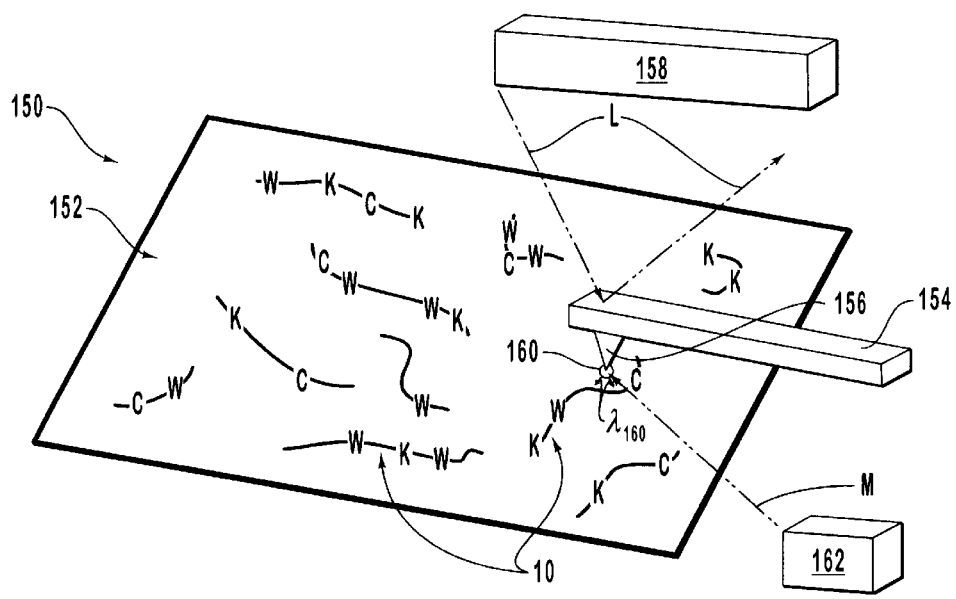
FIG. 16 is a perspective view of a second embodiment of an apparatus used according to teachings of the present invention to isolate a protein molecule from other protein molecules in a sample for the purpose of facilitating the determination of a fingerprint therefor.

FIG. 16 depicts a second embodiment of an apparatus used according to teachings of the present invention to isolate and characterize a protein molecule. The apparatus of FIG. 16 is an atomic force microscope 150. Individual protein molecules 10 are separately analyzed with atomic force microscope 150 due to the atomic resolution of atomic force microscope 150.

Protein molecules 10 are diluted and placed on a support 152 with distinct protein molecules 10 separated from one another. Support 152 is formed from a material, such as mica or glass, to which protein molecules 10 will adhere and upon which protein molecules 10 will be immobilized.

Atomic force microscope 150 has a cantilever 154 with a detector tip 156. As detector tip 156 is brought into proximity with a selected protein molecule 10, interactions between detector tip 156 and chemical structures of selected protein molecule 10 cause cantilever 154 to vibrate. The vibrations of cantilever 154 are measured by way of a laser detection system 158 that directs a laser beam L onto cantilever 154 and detects vibrations of laser beam L as the same is reflected by cantilever 154. The measurements are used to determine the molecular weight and length of selected protein molecule 10.

Detector tip 156 has attached thereto a fluorescent donor molecule 160. An excitation laser 162 directs a laser beam M toward detector tip 156 as detector tip 156 is scanned along the length of selected protein molecule 10. Laser beam M has a wavelength that excites fluorescent donor molecule 160 to produce emitted radiation $\lambda_{160}$ of a wavelength that will excite a chosen tagged amino acid residue, such as tagged amino acid residue C shown in various of protein molecules 10 on support 152. As donor molecule 160 on detector tip 156 is brought in an excited condition into proximity with amino acid residues C with fluorescent tags, emitted radiation $\lambda_{160}$ excites the tags. The excitation in selected of the tags on each amino acid residue C in selected protein molecule 10 causes detector tip 156 to vibrate, indicating the positions of each respective of the amino acid residues C along selected protein molecule 10.

Alternatively, the fluorescent donor molecule 160 on the detector tip 156 of the atomic force microscope 150 could be chosen so as to emit a wavelength of electromagnetic radiation that excites tryptophan amino acid residues of a protein molecule or that excites fluorescent tags on each of another type of amino acid residue of the protein molecule.

Figure 17:
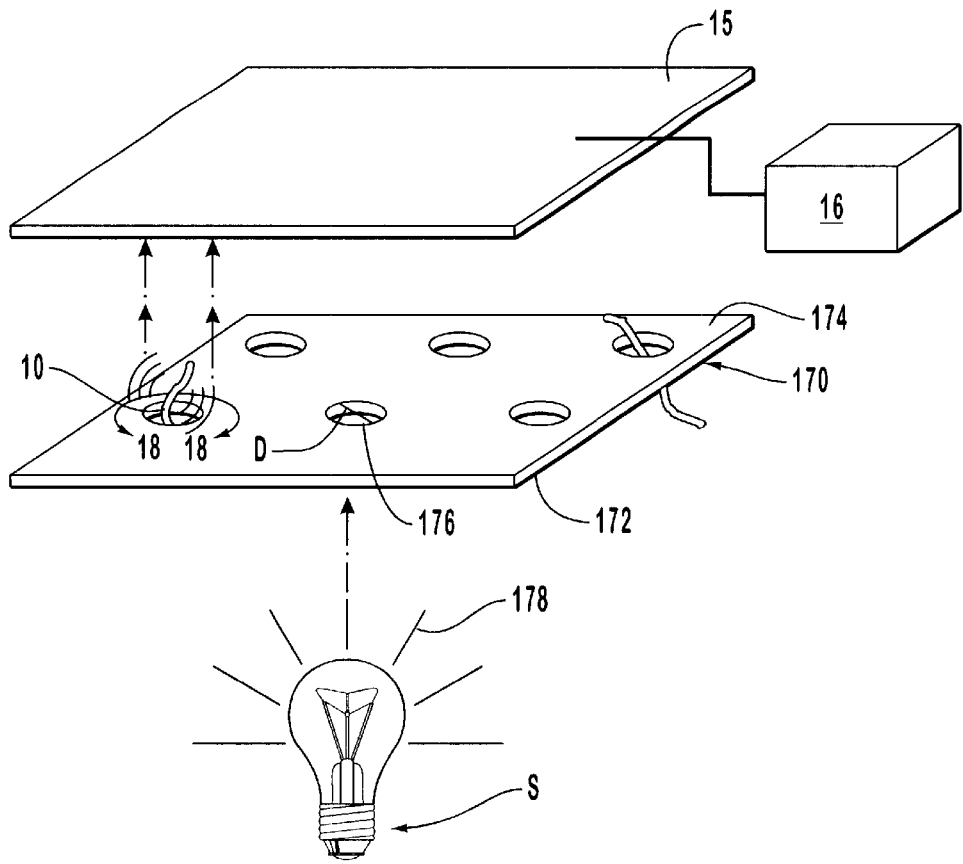
FIG. 17 is a perspective view of a third embodiment of an apparatus used according to teachings of the present invention to isolate a protein molecule from other protein molecules in a sample for the purpose of facilitating the determination of a fingerprint therefor.
Figure 18:
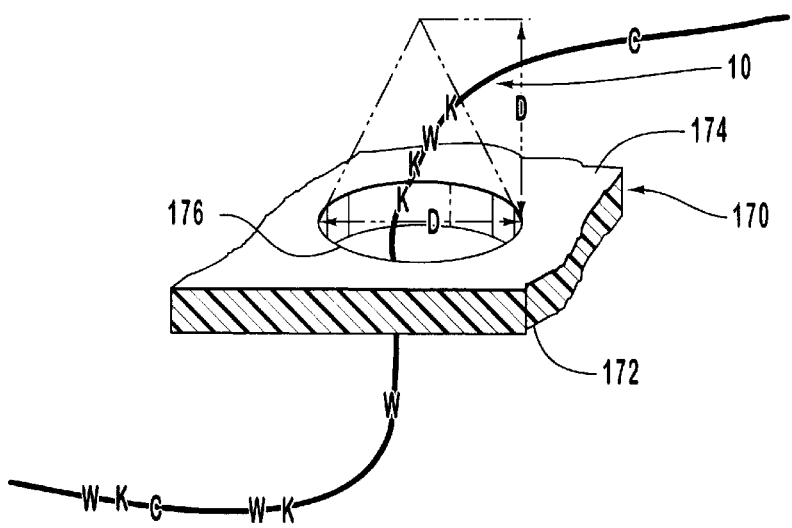
FIG. 18 is an enlarged perspective view of a portion of the apparatus depicted in FIG. 17.

A third embodiment of an apparatus that is useful for isolating and characterizing protein molecules according to teachings of the invention is shown in FIGS. 17 and 18.

FIG. 17 schematically illustrates an apparatus including a separation plate 170, a source S of electromagnetic radiation located on and directed toward a first side 172 of separation plate 170, and a detector 15 located on and facing an opposite, second side 174 of separation plate 170.

Separation plate 170 is a thin, planar structure with separation apertures 176 formed therethrough. Protein molecules 10 are propelled in solution or gel through apertures 176 by way of an electric field, a technique which is referred to in the art as electrophoresis. Each aperture 176 has a diameter D sized to permit a single linear protein molecule 10 to travel therethrough. For example, diameter D can be about 1–10 nm. The speed at which protein molecules 10 travel through apertures 176 depends on the applied electric field. Adjacent apertures 176 are spaced apart from one another so as to allow for optical resolution therebetween. For example, adjacent apertures 176 can be spaced about 1, 10, or 100 $\mu$m apart from each other. Separation plate 170 is formed from a material, such as silicon or plastic, that is opaque to visible wavelengths of electromagnetic radiation and that can be micromachined or otherwise modified by known processes to fabricate apertures 176 of desired diameter and spacing.

Source S emits electromagnetic excitation radiation 178 of wavelengths that will excite tryptophan amino acid residues or fluorescent tags on each of one or more other types of amino acid residues of protein molecules 10 passing through apertures 176. For example, the lysine and cysteine amino acid residues of protein molecules 10 could be labeled with different fluorescent tags and source S could emit a broad range of wavelengths of electromagnetic radiation to produce the spectrum depicted in FIG. 8.

Detector 15 is positioned to detect emitted radiation from amino acid residues of protein molecule 10 as protein molecule 10 exits specific aperture 18 among the several apertures 176 on second side 174 of separation plate 170. Electromagnetic radiation may be focused on detector 15 by way of an optical lens. Known apparatus that detect electromagnetic radiation, such as a charge coupled device (hereinafter "CCD") or an avalanche photodiode array, can be employed as detector 15. Detector 15 can simultaneously detect fluorescence emitted from amino acid residues or tags on the amino acid residues of different protein molecules 10. A processor 16 receives signals from detector 15 and generates data about the particular type of radiation detected.

FIG. 18 illustrates the phenomenon of "near field excitation" that occurs as protein molecules 10 that are exposed to electromagnetic radiation from source S on first side 172 of separation plate 170 travel through aperture 176. Diameter D is smaller than the wavelengths of excitation radiation 178 from source S and emitted radiation from stimulated amino acid residues W or fluorescent tags on amino acid residues K and C. Thus, excitation radiation and emitted radiation on first side 172 of separation plate 170 does not pass through aperture 176. As stimulated amino acid residue W or a stimulated tag on amino acid residue K or C exits aperture 176 on second side 174 of separation plate 170, however, amino acid residue W or the fluorescent tag remains excited by radiation from source S until leaving a substantially conical volume having a diameter D and an approximate height D. This near field excitation, the emitted radiation on second side 174 of separation plate 170, is detected by detector 15. The signals from detector 15 are then characterized by processor 16 as representing a specific type of amino acid residue which, when taken along with the speed at which a protein molecule travels through aperture 176, is located at a particular position along the length of protein molecule 10.

A fourth embodiment of apparatus that isolates and characterizes protein molecules in accordance with teachings of the present invention is illustrated in FIGS. 19–27.

Figure 19:
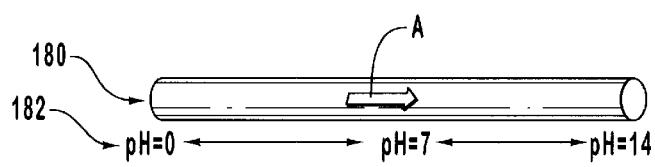
FIG. 19 is a schematic representation of an isoelectric focusing gel used in accordance with teachings of the present invention to isolate types of protein molecules in a sample of a plurality of types of protein molecules for the purpose of identifying the types of protein molecules in the sample.

FIG. 19 depicts an isoelectric focusing gel 180 used to isolate different types of protein molecules in a sample on the basis of the relative ratio of positively charged regions to negatively charged regions of each type of protein molecule. For each type of protein molecule, this ratio is referred to as the "isoelectric point." The process of isolating protein molecules on the basis of isoelectric points is referred to as "isoelectric focusing."

Prior to being introduced into isoelectric focusing gel 180, which has a web-like or matrix structure, the protein molecules are linearized to facilitate the travel of the protein molecules through the web of isoelectric focusing gel 180. The protein molecules can be linearized with known chemicals, such as those discussed above in reference to FIG. 9. When SDS, a negatively charged, or anionic, detergent is used to linearize the protein molecules, each of the protein molecules is given a net negative charge. The protein molecules can also be labeled with tags, in the same manner described above in reference to FIG. 9. Alternatively, the protein molecules can be labeled with tags after different types of protein molecules have been separated from each other.

Once the linearized protein molecules have been introduced into isoelectric focusing gel 180, isoelectric focusing gel 180 is placed in a pH gradient 182. Each protein molecule in isoelectric focusing gel 180 migrates in the direction of arrow A along the length of isoelectric focusing gel 180 to a pH that equals the isoelectric point of that protein molecule.

Isoelectric focusing can be used to isolate different types of protein molecules alone or in combination with other separation techniques. Typically, isoelectric focusing is the first step in a two-step separation process that is referred to as "two-dimensional" separation.

Figure 20:
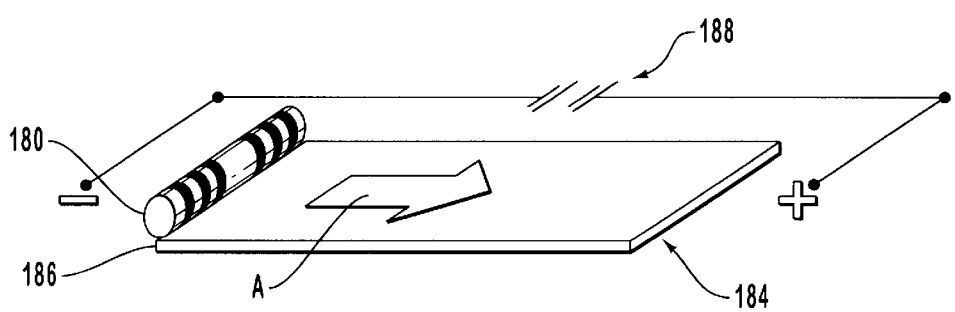
FIG. 20 is a schematic representation of an electrophoretic gel used according to teachings of the present invention to refine the isolation of types of protein molecules in a sample of a plurality of types of protein molecules previously separated from each other with the isoelectric focusing gel depicted in FIG. 19.

FIG. 20 illustrates the second step of two-dimensional separation, gel electrophoresis. In gel electrophoresis, native or linearized protein molecules are introduced into an electrophoresis gel 184. As depicted, the protein molecules that were previously separated in isoelectric focusing gel 180 are introduced into electrophoresis gel 184 at an edge 186 thereof. Like isoelectric focusing gel 180, electrophoresis gel 184 has a web-like structure. The passageways through electrophoresis gel 184 are, however, much smaller than the passageways through isoelectric focusing gel 180 so that the linearized protein molecules traveling through electrophoresis gel 184 are separated on the basis of size.

As an electric field 188 is applied to electrophoresis gel 184, the linearized protein molecules travel through electrophoresis gel 184 in the direction of arrow A. Smaller protein molecules travel more quickly than larger protein molecules through the passageways of electrophoresis gel 184.

Figure 21:
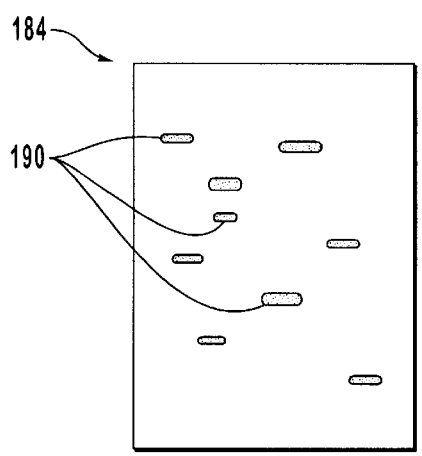
FIG. 21 is a schematic representation plan view of an electrophoretic gel after the various types of protein molecules in the sample have been separated from each other into respective bands in the manner illustrated in FIGS. 19 and 20.
Figure 22:
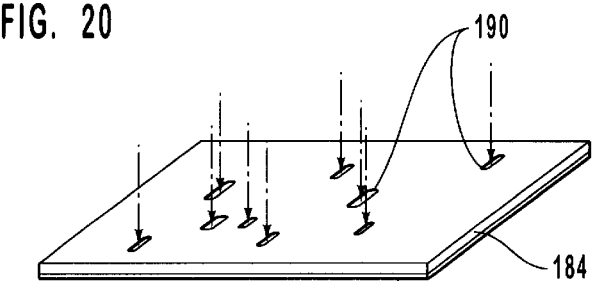
FIG. 22 is a schematic representation perspective view of a method for transferring the bands of the electrophoretic gel of FIG. 21 onto a membrane.
Figure 23:
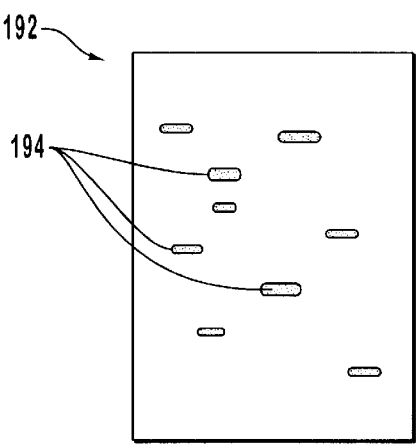
FIG. 23 is a schematic representation of the membrane of FIG. 22 after the bands of different types of protein molecules have been transferred thereto in the manner there illustrated.

FIG. 21 illustrates an electrophoresis gel 184 having separate bands 190 of different types of protein molecules therein. Next, as shown in FIG. 22, the protein molecules in bands 190 are transferred to a membrane 192 of a material such as a nitrocellulose filter or polyvinylidene difluoride, which is also referred to as "PVDF", or to another known solid support, such as a vinyl or nylon support, for further testing, a process referred to in the art as "blotting." FIG. 23 illustrates membrane 192 and the bands 194 of different types of protein molecules thereon. Each of bands 194 corresponds to a similarly located band 190 of electrophoresis gel 184 in FIG. 21.

The amino acid residues of the protein molecules in one or more of bands 194 can be labeled after being isolated on isoelectric focusing gel 180 and electrophoresis gel 184 and following the transfer of the protein molecules from bands 190 on electrophoresis gel 184 to membrane 192. The different types of protein molecules separated on membrane 192 are then characterized or identified and compared with one another.

Figure 24:
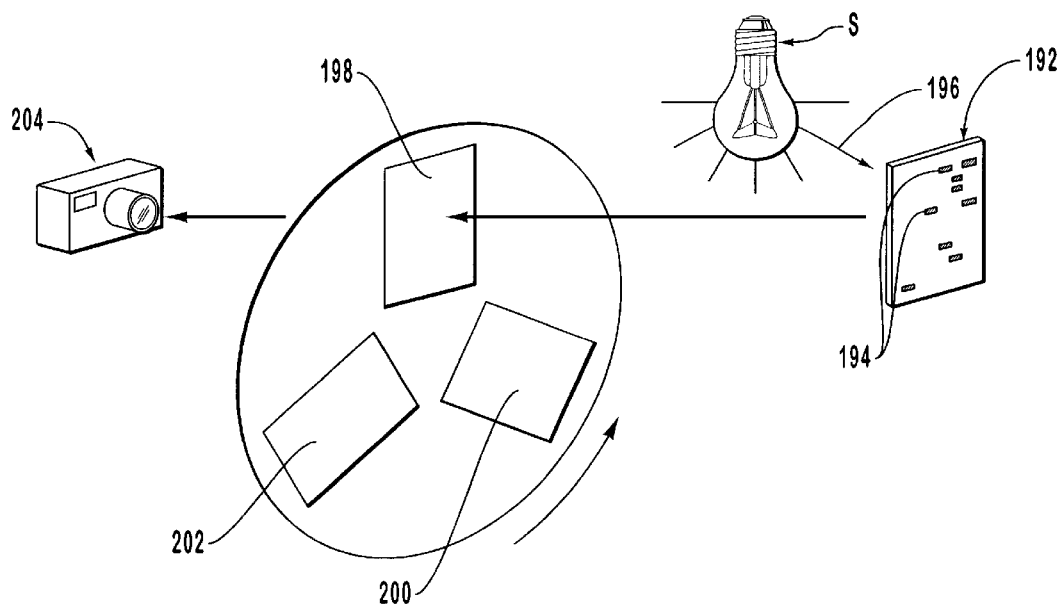
FIG. 24 is a schematic representation of an embodiment of a system used according to teachings of the present invention for identifying the types of protein molecules separated into respective bands in the electrophoretic gel of FIG. 21 and transferred to the membrane of FIG. 23.

As depicted in FIG. 24, when the protein molecules are labeled with fluorescent tags, electromagnetic excitation radiation 196 of one or more appropriate wavelengths can be directed from a source S toward membrane 192. As the tryptophan amino acid residues or different tags on one or more different types of amino residues are stimulated by excitation radiation 196, each of the tryptophan amino acid residues or tags emit radiation of a distinct wavelength range, in a manner similar to tryptophan amino acid residue W and the tags on amino acid residues K and C depicted in FIG. 8. The different ranges of wavelengths of emitted radiation can be separated from each other and from excitation radiation 196 by way of different optical filters 198, 200, 202 that permit only specific ranges of wavelengths of emitted radiation from amino acid residues W or from tags on amino acid residues K or C to pass therethrough.

When one optical filter 198 is used, the intensity of emitted radiation from a single type of amino acid residue or from the tags on a single type of amino acid residue can be. detected, in this case, by a camera 204. Camera 204 can be a digital camera that creates processable signals representative of the intensities of emitted radiation of different wavelengths or an optical camera.

Figure 25:
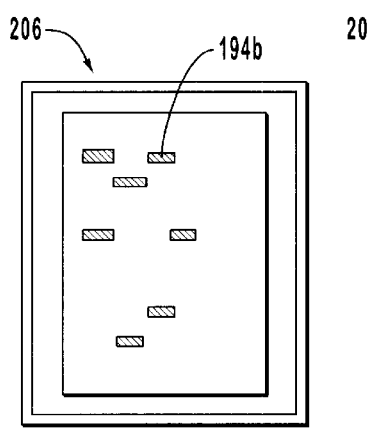
FIG. 25 is a schematic representation of a first photograph of the membrane of FIG. 24 obtained by use of the system shown in FIG. 24 and embodying data for determining a first fingerprint constituent for each of the types of proteins in the bands in the membrane of FIG. 24.
Figure 26:
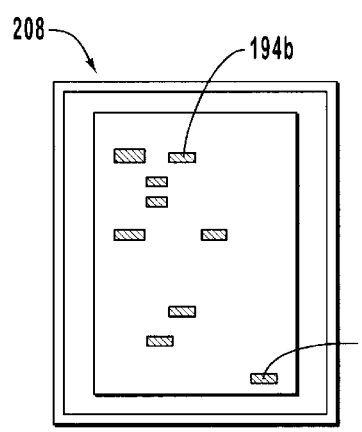
FIG. 26 is a schematic representation of a second photograph of the membrane shown in FIG. 24 embodying data for determining a second fingerprint constituent for each of the types of proteins in the bands in the membrane of FIG. 24.
Figure 27:
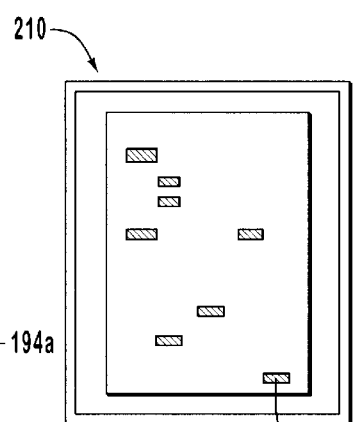
FIG. 27 is a schematic representation of a third photograph of the membrane shown in FIG. 24 embodying data for determining a third fingerprint constituent for each of the types of proteins in the bands in the membrane of FIG. 24.

FIGS. 25, 26, and 27 each illustrate a picture 206, 208, 210 of membrane 192 taken through a single optical filter 198, 200, 202, respectively. The intensity of emitted radiation of each band 194 in each wavelength range represents the number of a particular type of amino acid residue in the protein molecule isolated in that band 194 and provides a fingerprint constituent of the type of protein molecule in that band 194.

As illustrated, the protein molecules of some bands 194a and 194b do not give off a particular wavelength of emitted radiation. Bands 194a do not appear in picture 206 of FIG. 24 and band 194b does not appear in picture 210 of FIG. 27.

Figure 28:
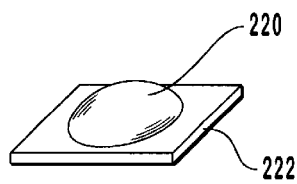
FIG. 28 is a perspective view of a cover slip for a microscope slide supporting a drop of a solution containing protein molecules.

FIGS. 28–33 depict a fifth embodiment of apparatus for isolating and characterizing a protein molecule. In the fifth embodiment, certain amino acid residues of protein molecules in a mixed sample are labeled with fluorescent tags in the manner described in reference to FIG. 9. The protein molecules of the mixed sample can optionally be linearized. The protein molecules in the mixed sample are separated from one another by diluting the sample. A drop 220 of the diluted sample is then placed on a microscope cover slip 222, as shown in FIG. 28.

Figure 29:
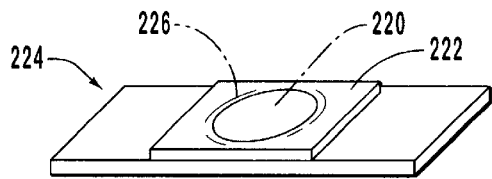
FIG. 29 is a perspective view of the cover slip depicted in FIG. 28 inverted and positioned on a microscope slide over a shallow recess therein, whereby the drop of solution hangs from the cover slip within the recess.

A microscope slide 224 with a recess 226 formed in a surface thereof is inverted over droplet 220 to enclose droplet 220 within recess 226 between microscope slide 224 and cover slip 222. FIG. 29 illustrates a microscope slide 224 prepared in this manner.

Figure 30:
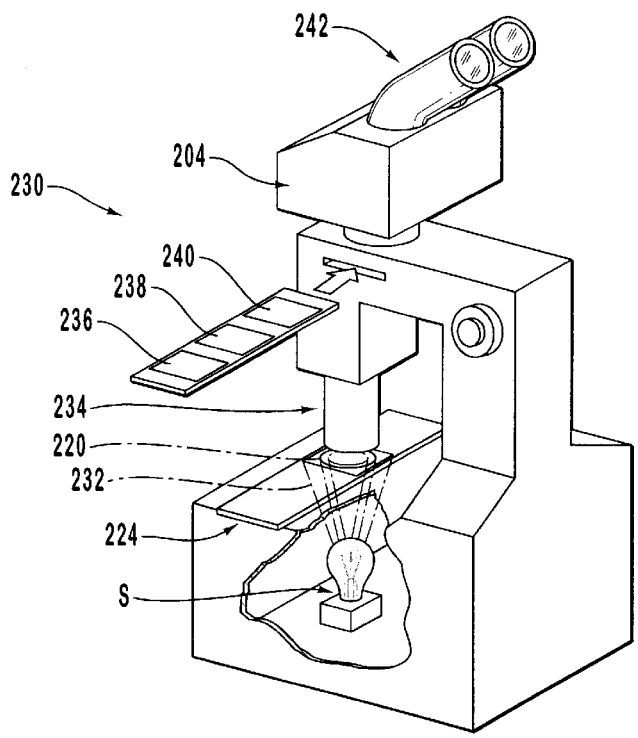
FIG. 30 is a perspective view of an apparatus used according to teachings of the present invention to obtain photographs of a field of view of a portion of the drop of solution in FIG. 29.

In FIG. 30, a fluorescence microscope 230 is used to detect the fluorescence of the tryptophan amino acid residues and of the fluorescent tags on amino acid residues of the protein molecules in droplet 220. Fluorescence microscope 230 has a source S of excitation radiation 232 directed toward droplet 220 held by microscope slide 224. Source S excites tryptophan amino acid residues and fluorescent tags on one or more other amino acid residues in the same manner as that depicted in FIG. 8.

Lens 234 of fluorescence micrscope 230 magnifies emitted radiation from tryptophan amino acid residues and from the fluorescent tags. The magnified emitted radiation from the tryptophan amino acid residues and the fluorescent tags on one or more other types of amino acid residues of the protein molecules in droplet 220 then passes through an optical filter 236, 238, 240 that permits only a specific range of wavelengths of emitted radiation from tryptophan amino acid residues or from the tags on other types of amino acid residues to pass therethrough. Optical filters 236, 238, and 240 screen out unwanted wavelengths of emitted radiation. When one optical filter 236 is used, the intensity of emitted radiation from a single type of amino acid residue or from the tags on a single type of amino acid residue can be detected, in this case, by a camera 204 or visually through an eyepiece 242 of fluorescence microscope 230.

Figure 31:
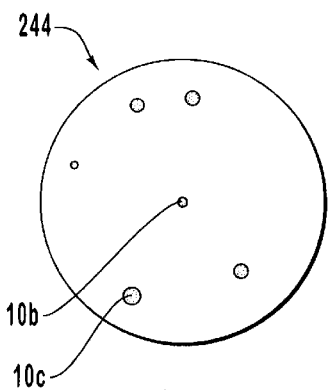
FIGS. 31–33 are schematic representations of a field of view of a portion of the drop of solution of FIG. 29 obtained by use of the apparatus of FIG. 30 using different filters, each field of view embodying data for determining fingerprints for the protein molecules appearing in that field of view.
Figure 32:
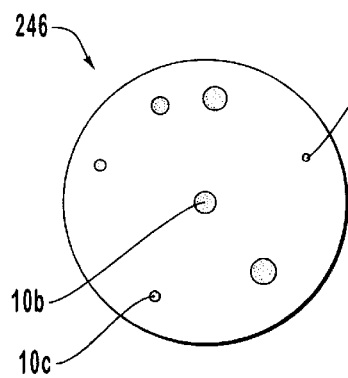
Figure 33:
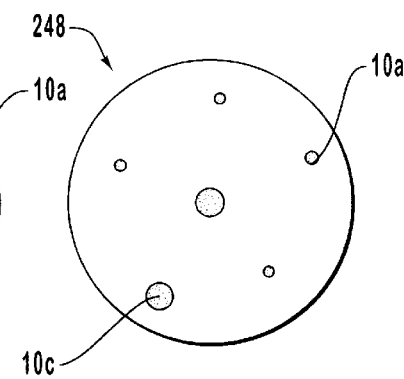

FIGS. 31–33 illustrate different fields of view of a portion of droplet 220 through fluorescence microscope 230. FIG. 31 depicts a field of view 244 through optical filter 236. FIG. 32 depicts a field of view 246 through optical filter 238. FIG. 33 depicts a field of view 248 through optical filter 240. As illustrated, protein molecules 10a emit radiation of some wavelengths and can, therefore, be seen in fields of view 246 and 248, but not in field of view 244. The intensities of emitted radiation from other protein molecules 10b also differ as protein molecules 10b are visualized through different filters. For example, the intensity of emitted radiation of a first wavelength from protein molecule 10b is greater in field of view 244 of FIG. 31 than the intensity of emitted radiation of a second wavelength from protein molecule 10b visualized in field of view 246 of FIG. 32 and than the intensity of emitted radiation of a third wavelength from protein molecule 10b in field of view 248 of FIG. 33, where protein molecule 10b does not appear to give off any emitted radiation of the third wavelength. Protein molecule 10c appears in each field of view 244, 246, 248.

The invention maybe embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for characterizing an unknown protein molecule, said method comprising the steps of:
 (a) isolating the unknown protein molecule;
 (b) linearizing the unknown protein molecule to produce a linearized unknown protein molecule;
 (c) labeling said linearized unknown protein molecule to produce a labeled linearized unknown protein molecule, said step of labeling comprising the steps of:
  (i) attaching a first tag to each first type of amino acid residue of said linearized unknown protein molecule, said first tag causing each first type of amino acid residue in said unknown protein molecule to produce a first emitted radiation at a corresponding first emission wavelength when said linearized unknown protein molecule is exposed to a first primary excitation radiation;
  (ii) attaching a second tag to each second type of amino acid residue of said linearized unknown protein molecule, said second tag causing each second type of amino acid residue in said linearized unknown protein molecule to produce a second emitted radiation at a corresponding second emission wavelength when said linearized unknown protein molecule is exposed to said first emitted radiation; and
 (d) ascertaining for the unknown protein molecule a characterization reflective of the physical structure of the unknown protein molecule as defined by the amino acid sequence thereof, said step of ascertaining comprising the steps of:
  (i) exposing said labeled linearized unknown protein molecule to said first primary excitation radiation;
  (ii) detecting emitted radiation from said labeled linearized unknown protein molecule caused by said step of exposing; and
  (iii) subjecting said emitted radiation from said labeled linearized unknown protein molecule to spectral analysis, thereby producing a spectral pattern thereof, said spectral pattern of said emitted radiation comprising:
   (A) a first spectral pattern component at said first emission wavelength reflective of the intensity of said first emitted radiation from said first tags attached to each first type of amino acid residue of said labeled linearized unknown protein molecule exposed to said first primary excitation radiation; and (B) a second spectral pattern component at said second emission wavelength reflective of the intensity of said second emitted radiation from said second tags attached to each second type of amino acid residue of said labeled linearized unknown protein molecule exposed to said first emitted radiation.

2. A method as recited in claim 1, wherein a detergent is utilized in said step of linearizing the unknown protein molecule.

3. A method as recited in claim 1, wherein sodium dodecyl sulfate is utilized in said step of linearizing the unknown protein molecule.

4. A method as recited in claim 1, wherein a chaotropic salt is utilized in said step of linearizing the unknown protein molecule.

5. A method as recited in claim 1, wherein said first tag comprises a fluorescent dye.

6. A method as recited in claim 1, wherein said step of detecting is performed with a charge coupled device.

7. A method as recited in claim 1, wherein in said step of attaching a first tag to each first type of amino acid residue of said linearized unknown protein molecule:

(a) a chemical precursor is utilized to attach said first tag to each first type of amino acid residue; and (b) said first tag is a metal tag.

8. A method as recited in claim 1, wherein said first type of amino acid residue in the unknown protein molecule comprises an amino acid residue selected from the group consisting of cysteine and lysine.

9. A method as recited in claim 1, wherein said step of isolating is performed using a hydrodynamic focusing apparatus.

10. A method as recited in claim 1, wherein said step of isolating is performed using:

(a) a separation plate opaque to light; and (b) apertures formed through said separation plate.

11. A method as recited in claim 10, wherein each of said apertures has a diameter in a range from about 1 nanometer to about 10 nanometers.

12. A method as recited in claim 10, wherein said separation plate is formed from a material selected from the group consisting of silicon and opaque plastics.

13. A method as recited in claim 1, wherein said step of isolating is performed using an electrophoresis gel.

14. A method as recited in claim 1, wherein said step of isolating is performed using a dilute solution.

15. A method as recited in claim 1, wherein:

(a) said second tag attached to each second type of amino acid residue of said linearized unknown protein molecule additionally causes each second type of amino acid residue in said linearized unknown protein molecule to produce a third emitted radiation at a corresponding third emission wavelength when said linearized unknown protein molecule is exposed to a second primary excitation radiation;

(b) the step of ascertaining further comprises exposing said labeled linearized unknown protein molecule to said second primary excitation radiation; and (c) said spectral pattern of said emitted radiation further comprises a third spectral pattern component at said third emission wavelength reflective of the intensity of said third emitted radiation from said second tags attached to each second type of amino acid in said linearized unknown protein molecule exposed to said second primary excitation radiation.

16. A method for characterizing an unknown protein molecule having at least one of a first type of amino acid residue and at least one of a second type of amino acid residue, the first type of amino acid residue in the unknown protein molecule being a tryptophan amino acid residue and being, therefore, capable of producing a first emitted radiation of a corresponding first emission wavelength when exposed to a first primary excitation radiation, and the second type of amino acid residue in the unknown protein molecule being a second amino acid residue different from tryptophan, said method comprising the steps of:

(a) isolating the unknown protein molecule; and (b) labeling each second type of amino acid residue in the unknown protein molecule with a tag to create a labeled unknown protein molecule, said tag causing each second type of amino acid residue of the unknown protein molecule to produce a second emitted radiation at a corresponding second emission wavelength:

(i) when said tag is exposed to the first emitted radiation, and (ii) when said tag is exposed to a second primary excitation radiation of the first emission wavelength;

(c) ascertaining for the unknown protein molecule a characterization reflective of the physical structure of the unknown protein molecule as defined by the amino acid sequence thereof, said step of ascertaining comprising the steps of:

(i) exposing said labeled unknown protein molecule to the first primary excitation radiation and to said second primary excitation radiation;

(ii) detecting emitted radiation from said labeled unknown protein molecule caused by said step of exposing; and (iii) subjecting said emitted radiation from said labeled unknown protein molecule to spectral analysis, thereby producing a spectral pattern thereof, said spectral pattern of said emitted radiation comprising:

(A) a first spectral pattern component at said first emission wavelength reflective of the intensity of the first emitted radiation from the tryptophan amino acid residues of said labeled unknown protein molecule exposed to the first primary excitation radiation; and (B) a second spectral pattern component at said second emission wavelength reflective of the intensity of said second emitted radiation from said tag attached to each second type of amino acid residue of said labeled unknown protein molecule exposed to the first emitted radiation and to said second primary excitation radiation.

17. A method as recited in claim 16, further comprising the step of linearizing the unknown protein molecule.

18. A method as recited in claim 17, wherein said step of linearizing precedes said step of isolating.

19. A method as recited in claim 17, wherein said step of linearizing precedes said step of labeling.

20. A method as recited in claim 16, wherein said step of isolating is performed using a hydrodynamic focusing apparatus.

21. A method as recited in claim 16, wherein said step of isolating is performed using:

(a) a separation plate opaque to light; and (b) apertures formed through said separation plate.

22. A method as recited in claim 21, wherein each of said apertures has a diameter in a range from about 1 nanometer to about 10 nanometers.

23. A method as recited in claim 21, wherein said separation plate is formed from a material selected from the group consisting of silicon and opaque plastics.

24. A method as recited in claim 16, wherein said step of isolating is performed using an electrophoresis gel.

25. A method as recited in claim 16, wherein said step of isolating is performed using a dilute solution.

26. A method as recited in claim 17, wherein a detergent is utilized in said step of linearizing.

27. A method as recited in claim 26, wherein sodium dodecyl sulfate is utilized in said step of linearizing.

28. A method as recited in claim 17, wherein a chaotropic salt is utilized in said step of linearizing.

29. A method as recited in claim 16, wherein said step of exposing said labeled unknown protein molecule to the first primary excitation radiation and to said second primary excitation radiation comprises the following steps:
  (a) illuminating said labeled unknown protein molecule with the first primary excitation radiation; and
  (b) simultaneously with said step (a) illuminating said labeled unknown protein molecule with said second primary excitation radiation.

30. A method as recited in claim 15, wherein said step of exposing said labeled linearized unknown protein molecule to said first primary excitation radiation and said step of exposing said labeled linearized unknown protein molecule to said second primary excitation radiation are performed simultaneously.

31. A method for characterizing a selected protein molecule in a sample containing a plurality of protein molecules, said method comprising the steps of:
  (a) isolating the selected protein molecule from other protein molecules in the sample;
  (b) labeling the selected protein molecule to produce a labeled selected protein molecule, said step of labeling comprising the step of:
    (i) attaching a first tag to each first type of amino acid residue in the selected protein molecule, said first tag causing each first type of amino acid residue in the selected protein molecule to produce a first emitted radiation at a corresponding first emission wavelength when the selected protein molecule is exposed to a first primary excitation radiation;
    (ii) attaching a second tag to each second type of amino acid residue in the selected protein molecule, said second tag causing each second type of amino acid residue in the selected protein molecule to produce a second emitted radiation at a corresponding second emission wavelength when the selected protein molecule is exposed to a second primary excitation radiation; and
  (c) ascertaining for the selected protein molecule a characterization reflective of the physical structure of the selected protein molecule as defined by the amino acid sequence thereof, said step of ascertaining comprising:
    (i) exposing said labeled selected protein molecule to said first primary excitation radiation and to said second primary excitation radiation;
    (ii) detecting emitted radiation from said labeled selected protein molecule caused by said step of exposing; and
    (iii) subjecting said emitted radiation from said labeled selected protein molecule to spectral analysis to produce a spectral pattern thereof, said spectral pattern of said emitted radiation comprising:
      (A) a first spectral pattern component at said first emission wavelength reflective of the intensity of said first emitted radiation from said first tags attached to each first type of amino acid residue of said labeled selected protein molecule exposed to said first primary excitation radiation; and
      (B) a second spectral pattern component at said second emission wavelength reflective of the intensity of said second emitted radiation from said second tags attached to each second type of amino acid residue of said labeled selected protein molecule exposed to said second primary excitation radiation.

32. A method as recited in claim 31, wherein said first tag comprises a fluorescent dye.

33. A method as recited in claim 31, wherein in said step of attaching a first tag to each first type of amino acid residue:
  (a) a chemical precursor is utilized to attach said first tag to each first type of amino acid residue; and
  (b) said first tag is a metal tag.

34. A method as recited in claim 31, wherein said first type of amino acid residue in the selected protein molecule comprises an amino acid residue selected from the group consisting of cysteine and lysine.

35. A method as recited in claim 31, wherein said step of isolating is performed using a hydrodynamic focusing apparatus.

36. A method as recited in claim 31, wherein said step of isolating is performed using:
  (a) a separation plate opaque to light; and
  (b) apertures formed through said separation plate.

37. A method as recited in claim 36, wherein each of said apertures has a diameter in a range from about 1 nanometer to about 10 nanometers.

38. A method as recited in claim 36, wherein said separation plate is formed from a material selected from the group consisting of silicon and opaque plastics.

39. A method as recited in claim 31, wherein said step of isolating is performed using an electrophoresis gel.

40. A method as recited in claim 31, wherein said step of isolating is performed using a dilute solution.

41. A method as recited in claim 31, wherein said step of exposing said labeled selected protein molecule to said first primary excitation radiation and to said second primary excitation radiation comprises the steps of:
  (a) illuminating said labeled selected protein molecule with said first primary excitation radiation; and
  (b) simultaneously with said step (a) illuminating said labeled selected protein molecule with said second primary excitation radiation.

42. A method for characterizing a selected protein molecule in a sample containing a plurality of protein molecules, the selected protein molecule having at least one of a first type of amino acid residue, at least one of a second type of amino acid residue, and at least one of a third type of amino acid residue, the first type of amino acid residue in the selected protein molecule being a tryptophan amino acid residue and being, therefore, capable of producing a first emitted radiation of a corresponding first emission wavelength when exposed to a first excitation radiation, the second type of amino acid residue and the third type of amino acid residue in the selected protein molecule being amino acid residues different from tryptophan and from each other, and said method comprising the steps of:

(a) isolating the selected protein molecule from other protein molecules in the sample;
(b) labeling the selected protein molecule to produce a labeled selected protein molecule, said step of labeling comprising the step of:
  (i) attaching a first tag to each second type of amino acid residue in the selected protein molecule, said first tag causing each second type of amino acid residue in the selected protein molecule to produce a second emitted radiation at a corresponding second emission wavelength:
    (A) when said first tag is exposed to the first emitted radiation; and
    (B) when said first tag is exposed to a second primary excitation radiation at said first excitation wavelength; and
  (ii) attaching a second tag to each third type of amino acid residue in the selected protein molecule, said second tag causing each third type of amino acid residue in the selected protein molecule to produce a third emitted radiation at a corresponding third emission wavelength:
    (A) when said second tag is exposed to said second emitted radiation; and
    (B) when said second tag is exposed to a third primary excitation radiation at said second emission wavelength; and
(c) ascertaining for the selected protein molecule a characterization reflective of the physical structure of the selected protein molecule as defined by the amino acid sequence thereof, said step of ascertaining comprising the steps of:
  (i) exposing said labeled selected protein molecule to the first primary excitation radiation, said second primary excitation radiation, and said third primary excitation radiation;
  (ii) detecting emitted radiation from said labeled selected protein molecule caused by said step of exposing; and
  (iii) subjecting said emitted radiation from said labeled selected protein molecule to spectral analysis, thereby producing a spectral pattern thereof, said spectral pattern of said emitted radiation comprising:
    (A) a first spectral pattern component at said first emission wavelength reflective of the intensity of said first emitted radiation from the tryptophan amino acid residue of the labeled selected protein molecule exposed to the first primary excitation radiation;
    (B) a second spectral pattern component at said second emission wavelength reflective of the intensity of said second emitted radiation from said first tag attached to each second type of amino acid residue of the labeled selected protein molecule exposed to the first emitted radiation and to said second primary excitation radiation; and
    (C) a third spectral pattern component at said third emission wavelength reflective of the intensity of said second emitted radiation from said second tag attached to each third type of amino acid residue of the labeled selected protein molecule exposed to said second emitted radiation and to said third primary excitation radiation.

43. A method as recited in claim 42, wherein said step of isolating is performed using a hydrodynamic focusing apparatus.

44. A method as recited in claim 42, wherein said step of isolating is performed using:

(a) a separation plate opaque to light; and
(b) apertures formed through said separation plate.

45. A method as recited in claim 44, wherein each of said apertures has a diameter in a range from about 1 nanometer to about 10 nanometers.

46. A method as recited in claim 44, wherein said separation plate is formed from a material selected from the group consisting of silicon and opaque plastics.

47. A method as recited in claim 42, wherein said step of isolating is performed using an electrophoresis gel.

48. A method as recited in claim 42, wherein said step of isolating is performed using a dilute solution.

49. A method as recited in claim 42, wherein said step of exposing said labeled selected protein molecule to the first primary excitation radiation, said second primary excitation radiation, and said third primary excitation radiation comprises the steps of:
  (a) illuminating said labeled selected protein molecule with the first primary excitation radiation;
  (b) simultaneously with said step (a) illuminating said labeled selected protein molecule with said second primary excitation radiation; and
  (c) simultaneously with said step (b) illuminating said labeled selected protein molecule with said third primary excitation radiation.

50. A method for characterizing an unknown protein molecule having at least one of a first type of amino acid residue, at least one of a second type of amino acid residue, and at least one of a third type of amino acid residue, the first type of amino acid residue in the unknown protein molecule being a tryptophan amino acid residue and being, therefore, capable of producing a first emitted radiation of a corresponding first emission wavelength when exposed to a first excitation radiation, the second type of amino acid residue and the third type of amino acid residue in the unknown protein molecule being amino acid residues different from tryptophan and from each other, and said method comprising the steps of:
  (a) isolating the unknown protein molecule;
  (b) linearizing the unknown protein molecule to produce a linearized unknown protein molecule;
  (c) labeling the linearized unknown protein molecule to produce a labeled linearized unknown protein molecule, said step of labeling comprising the steps of:
    (i) attaching a first tag to each second type of amino acid residue in said linearized unknown protein molecule, said first tag causing each second type of amino acid residue in said linearized unknown protein molecule to produce a second emitted radiation at a corresponding second emission wavelength:
      (A) when said first tag is exposed to the first emitted radiation; and
      (B) when said first tag is exposed to a second primary excitation radiation of the first emission wavelength;
    (ii) attaching a second tag to each third type of amino acid residue in the linearized unknown protein molecule, said second tag causing each third type of amino acid residue in the linearized unknown protein molecule to produce a third emitted radiation at a corresponding third emission wavelength when said second tag is exposed to said second emitted radiation; and
  (d) ascertaining for the unknown protein molecule a characterization reflective of the physical structure of the unknown protein molecule as defined by the amino acid sequence thereof, said step of ascertaining comprising the steps of:
(i) exposing said labeled linearized unknown protein molecule to the first primary excitation radiation and said second primary excitation radiation;
(ii) detecting emitted radiation from said labeled linearized unknown protein molecule caused by said step of exposing; and
(iii) subjecting said emitted radiation from said labeled linearized unknown protein molecule to spectral analysis, thereby producing a spectral pattern thereof, said spectral pattern of said emitted radiation comprising:
 (A) a first spectral pattern component at said first emission wavelength reflective of the intensity of the first emitted radiation from the tryptophan amino acid residues of said labeled linearized unknown protein molecule exposed to the first primary excitation radiation;
 (B) a second spectral pattern component at said second emission wavelength reflective of the intensity of said second emitted radiation from said first tag attached to each second type of amino acid residue of said labeled linearized unknown protein molecule exposed to the first emitted radiation and said second primary excitation radiation; and
 (C) a third spectral pattern component at said third emission wavelength reflective of the intensity of said third emitted radiation from said second tag attached to each third type of amino acid residue of said labeled linearized unknown protein molecule exposed to said second emitted radiation.

51. A method as recited in claim 50, wherein said step of exposing said labeled linearized unknown protein molecule to the first primary excitation radiation and said second primary excitation radiation comprises the steps of:
(a) illuminating said labeled linearized unknown protein molecule with the first primary excitation radiation; and
(b) simultaneously with said step (a) illuminating said labeled linearized unknown protein molecule with said second primary excitation radiation.

* * * * *

UNITED STATES PATENT AND TRADEMARK OFFICE
CERTIFICATE OF CORRECTION

PATENT NO.    : 6,569,685 B1
DATED         : May 27, 2003
INVENTOR(S)   : Carlson et al.

It is certified that error appears in the above-identified patent and that said Letters Patent is hereby corrected as shown below:

Title page,
Item [75], Inventors, after "Robert H. Carlson" change "Union City, CA" to -- Seattle, WA --; after "Ian E. Burbulis" change "Kensington" to -- Berkley --;
Item [56], References Cited, OTHER PUBLICATIONS, "Glazer, A.N." reference, change "Site Specific" to -- Site-Specific --; "Guttfman, A.," reference, change "Protien" to -- Proteins --; "Miller, J.H." reference, change "Galacosidase" to -- Galactosidase --; "Meldal, Morten" reference, "Solid Phase" to -- Solid-Phase --; "White, Frederick H. Jr.," reference, change "on" to -- of --;
"Wong, Shan S.," reference, change "Protien" to -- Protein --;

Drawings:
Figure 33, delete the stippled, circular spot at the center of field of view 248:
Replace Figure 31 with the following:
--                                                    --

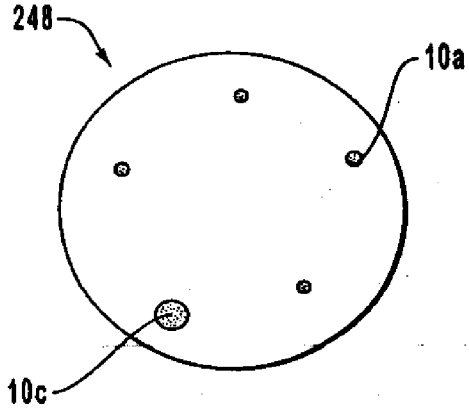

FIG. 33

Column 1,
Line 10, change "readily-detectable" to -- readily detectable --;

Column 2,
Line 37, change "bases" to -- basis --;

Column 3,
Line 7, after "molecule" change "are" to -- is --;
Line 30, after "that" change "are" to -- is --;
Line 47, change "$\lambda_{KC}$" to -- $\lambda_{SK}$ --;

UNITED STATES PATENT AND TRADEMARK OFFICE
CERTIFICATE OF CORRECTION

PATENT NO. : 6,569,685 B1
DATED : May 27, 2003
INVENTOR(S) : Carlson et al.

It is certified that error appears in the above-identified patent and that said Letters Patent is hereby corrected as shown below:

Column 4,
Line 27, after "in" insert -- a --;
Line 27, after "protein" insert -- of --;

Column 8,
Line 16, after "sequence" insert -- peptide 11 inches --;
Line 17, after "W," change "and" to -- an --;
Line 17, after "12," change "in" to -- and --;
Line 40, delete the period after "in";
Line 60, change "First" to -- first --;

Column 9,
Line 40, before "excitation" insert -- electromagnetic --;

Column 12,
Line 1, change "first" to -- third --;

Column 16,
Lines 31-32, delete "in selected";

Column 17,
Line 12, change "specific aperture 18 among the several" to -- one of --;

Column 18,
Line 62, delete "each of";
Line 63, after "or" insert -- the different --;

Column 19,
Line 7, delete the period after "be";
Line 22, change "Bands" to -- band --;
Line 22, change "do" to -- does --;
Line 23, change "24" to -- 25, --;
Line 31, change "drop" to -- droplet --;
Line 48, change "micrscope" to -- microscope --;

Column 20,
Line 10, change "244" to -- 248 --;
Line 10, change "31" to -- 32 --;
Line 12, change "246" to -- 244 --;
Line 12, change "32" to -- 31 --;

UNITED STATES PATENT AND TRADEMARK OFFICE
CERTIFICATE OF CORRECTION

PATENT NO. : 6,569,685 B1
DATED : May 27, 2003
INVENTOR(S) : Carlson et al.

It is certified that error appears in the above-identified patent and that said Letters Patent is hereby corrected as shown below:

Column 20, (cont'd),
Line 15, change "to give off any emitted" to -- at all. --;
Line 16, delete "radiation of the third wavelength.";
Line 17, after "each" insert -- of --; and
Line 17, change "field" to -- fields --.
Line 38, after "said" insert -- linearized --;
Line 42, after "radiation;" insert -- and --;

Column 21,
Line 25, change "with" to -- using --;

Column 23,
Line 39, change "step" to -- steps --;
Line 46, after "radiation;" insert -- and --;

Signed and Sealed this

Thirty-first Day of May, 2005

JON W. DUDAS
*Director of the United States Patent and Trademark Office*